(12) United States Patent
Kutchan et al.

(10) Patent No.: US 7,193,127 B1
(45) Date of Patent: Mar. 20, 2007

(54) CODEINONE REDUCTASE FROM ALKALOID POPPY

(75) Inventors: Toni M. Kutchan, Munich (DE); Meinhard H. Zenk, Munich (DE); David G. Atkins, New York, NY (US); Anthony J. Fist, Norwood (AU)

(73) Assignee: Johnson & Johnson Research Pty. Limited (AU)

( * ) Notice: Subject to any disclaimer, the term of this patent is extended or adjusted under 35 U.S.C. 154(b) by 0 days.

(21) Appl. No.: 09/937,665

(22) PCT Filed: Mar. 24, 2000

(86) PCT No.: PCT/AU00/00249

§ 371 (c)(1),
(2), (4) Date: Feb. 20, 2002

(87) PCT Pub. No.: WO00/58333

PCT Pub. Date: Oct. 5, 2000

(30) Foreign Application Priority Data

Mar. 26, 1999 (AU) .................. PP9463

(51) Int. Cl.
*C12N 15/29* (2006.01)
*C12N 15/52* (2006.01)
*C12N 15/63* (2006.01)
*C12N 15/82* (2006.01)
*A01H 1/00* (2006.01)

(52) U.S. Cl. ............. 800/278; 435/6; 435/69.1; 435/252.3; 435/320.1; 435/419; 435/468; 536/23.1; 536/23.2; 536/23.6; 800/281; 800/298; 800/323; 530/350; 530/370

(58) Field of Classification Search ............ 435/6, 435/69.1, 468, 419, 252.3, 320.1; 530/370; 536/23.6; 800/278, 295
See application file for complete search history.

(56) References Cited

U.S. PATENT DOCUMENTS 4,801,540 A * 1/1989 Hiatt et al. ............. 435/411

FOREIGN PATENT DOCUMENTS

WO       00/00249      10/2000

OTHER PUBLICATIONS

Yun et al. Proc. Natl. Acad. Sci. USA 89(24): 11799-11803 (Dec. 1992).*
Liscombe et al Evidence For The Monophyletic Evolution of Benzylisoquinoline Alkaloid Biosynthesis In Angiosperms. Photochemistry. Oct. 2005;66(20):2501-20, 2513.*
Nailish Samanani and Peter J. Facchini Purification and Characterization of Norcoclaurine Synthase The First Committed Enzyme in Benzylisoquinoline Alkaloid Biosynthesis in Plants J. Biol. Chem., vol. 277, Issue 37, 33878-33883, Sep. 13, 20022.*
Millgate et al, Morphine-pathway block in top1 poppies. Nature 431: 413-414.*
Lazar et al. (1988) Transforming Growth Factor α: Mutation of Aspartic Acid 47 and Leucine 48 in Different Biological Activities. Molec. & Cell. Biol. 1247-52.*
Lenz et al (1995) Stereoselective reduction of codeinone, the penultimate enzymatic step during morphine biosynthesis in *Papaver somniferum* Tetrahedron lett. 36(14)) 2449-2452.*
Lenz et al (1995) Purification and properties of codeinone reductase (NADPH) from *Papaver somniferum* Eur. J. Biochem. 233 (1) 132-9.*
Unterlinner B; Lenz R; Kutchan T M Molecular cloning and functional expression of codeinone reductase: the penultimate enzyme in morphine biosynthesis in the opium poppy *Papaver somniferum* Plant journal : for cell and molecular biology, (Jun. 1999) 18 (5) 465-75.*
van de Loo et al (1995) An Oleate 12-Hydroxylase From *Ricinus communis* L. Is A Fatty Acyl Desaturase Homolog. P.N.A.S. 92:6743-47.*
Broun, et al (1998) Catalytic Plasticity Of Fatty Acid Modification Enzymes Underlying Chemical Diversity Of Plant Lipids. Science 282(13) 1315-1317.*
Sweetlove et al (1996) Starch Metabolism In Tubers Of Transgenic Potato (*Solanum tuberosum*) With Increased Adp-Glucose Pyrophosphorylase Biochem J. 30:493-98.*
Doerks, et al (1998) Protein Annotation: Detective Work For Function Prediction TIG 14(6) 248-250.*
Tsukaya, et al, (1991) Sugar Dependent Expression of the chs-A gene for chalcone synthase from Petunia in Transgenic *Arabidopsis*. Plant Physiol. 97:1414-21.*
van der Krol et al Flavonoid Genes in Petunia . . . The plant Cell vol. 2, 291-99 Apr. 1990.*
Welle R., Schroeder G., Schiltz E., Grisebach H., Schroeder J.; "Induced plant responses to pathogen attack. Analysis and heterologous expression of the key enzyme in the biosynthesis of phytoalexins in soybean (Glycine max L. Merr. cv. Harosoy 63)."; Eur. J. Biochem. 196:423-430(1991).*
Stratagene Catalog, pCAL vector series (2006).*
Promega Catalog, pGEM vector series (2006).*

(Continued)

*Primary Examiner*—David T. Fox
*Assistant Examiner*—Brendan O. Baggot
(74) *Attorney, Agent, or Firm*—Paul Burgess

(57) ABSTRACT

The present invention concerns codeinone reductase from alkaloid poppy plants, the polynucleotides encoding the enzyme, transgenic plants transformed or transfected with polynucleotide(s) encoding codeinone reductase and to the production of alkaloids from transformed or transfected poppy plants.

27 Claims, 11 Drawing Sheets

OTHER PUBLICATIONS

Invitrogen Life Technologies, Instruction Manual, Guide to baculovirus expresion vector systems (BEVS) and insect culture techniques, pp. 1-23 and Figure depicting pFastBac1 (2002).*

Unterlinner, B et al., "Molecular cloning and functional expression of codeinone reductase: the penultimate enzyme in morphine biosynthesis in the opium poppy *Papaver somniferum*". Plant Journal, Jun. 1999, vol. 18, No. 5 pp. 465-475.

Lenza, R. et al, "Purification and properties of codeinone reductase (NADPH) from *Papaver somniferum* cell cultures and differentiated plants". European Journal of Biochemistry, Oct. 1, 1995, vol. 233, No. 1, pp. 132-139.

Decker Gabriele et al: "Characterization of proteins in latex of the opium poppy (*Papaver somniferum*) using two-dimensional gel electrophoresis and microsequencing." ELECTROPHORESIS, vol. 21, No. 16, Oct. 2000 pp. 3500-3516. XP001087804.

Huang F-C et al: "Distribution of morphinan and benxo'Cphenanthridine alkaloid gene transcript accumulation in *Papaver somniferum*" Phytochemistry, Pergamon Press, GB, vol. 53, No. 5, Mar. 1, 2000 pp. 555-564, XP004291339.

Kutchan Toni M: "Molecular genetics of plant alkaloid biosynthesis", Alkaloids (Academic Press) (1998), 50, 257-316 XP001069571.

International Search Report for Application No. 00910437.3 dated Jul. 12, 2002.

* cited by examiner

SCHEME I

Fig 2

| | |
|---|---|
| Peptide 3 | X L Q E L M A |
| Peptide 7 | V L H Q I A V A R G K |
| Peptide 14 | D D D E L F I T S K |
| Peptide 16 | I P D V V N Q V E M S P T L G Q |
| Peptide 17 | X V N E I P K |
| Peptide 25 | X V A Q V |
| Peptide 29 | I F D N X L T A E D |

Fig 3

```
             51                                                          90
Alfalfa      KQGYRHFDTA AAYGSEQALG EALKEAIELG LVTREELFVT
Glycyrrh.    KQGYRHFDTA AAYGSETALG EALKEARDLG LVTREELFVT
Soybean      KQGYRHFDTA AAYGSEQALG EALKEAIHLG LVSRQDLFVT
Opium poppy  .......... .......... .......... .....ELFIT 91                                                          140
SKLWVTENHP HLVIPALQKS LKTLQLDYLD LYLIHWPLSS QPGKFSFPID
SKLWVTENHP HLVIPALRKS LETLQLEYLD LYLIHWPLSS QPGKFSFPIQ
SKLWVTENHP HLVLPALRKS LKTLQLEYLD LYLIHWPLSS QPGKFSFPIE
SK........ .......... .......... .......... ..........

141                                                         190
VADLLPFDVK GVWESMEESL KLGLTKAIGV SNFSVKKLEN LLSVATVLPA
VEDLLPFDVK GVWESMEECL KLGLTKAIGV SNFSVKKLQN LLSVATIRPA
VEDLLPFDVK GVWESMEECQ KLGLTKAIGV SNFSVKKLQN LLSVATIRPV
.......... .......... .......... .......LQE LMA...IPDV 191                                                         240
VNQVEMN... LAWQQKKLRE FCNANGIVLT AFSPLRKGAS RGPNEVMEND
VNQVEMN... LAWQQKKLRE FCTANGIVLT AFSPLRKGAS RGPNEVMEND
VDQVEMN... LAWQQKKLRE FCKENGIIVT AFSPLRKGAS RGPNEVMEND
VNQVEMSPTL .......... .......... .......... ..........

241
MLKEIADAHG KSVAQISLRW LYEQGVTFVP KSYDKERMNQ NLC
MLKGIAEAHG KSIAQVSLRW LYEQGVTFVA KSYDKERMNQ NLQ
VLKEIAEAHG KSIAQVSLRW LYEQGVTFVP KSYDKERMNQ NLH
VLHQIAVARG K......... .....VNEIP K......... ...
```

Fig 4

```
corl.1    .MESNGVPMI  TLSSG...IR  MPALGMGTAE  TMVKGTEREK  LAFLKAIEVG
corl.2    .---------  ----------  -------V-   --E-------  ----N-----
corl.3    .---------  ----------  ----------  ----------  ----------
corl.4    .---------  ----------  ----------  ----------  ----------
6'dcs     MAAAIEI-T-  VFPNSSAQQ-  --VV---S-P  DFTCKKDT.-  E-IIE-VKQcorl.1    YRHFDTAAAY  QTEECLGEAI  AEALQLGLIK  SRDELFITSK  LWCADAHADL
corl.2    ----------  -S--------  ----------  ----------  ----------
corl.3    ----------  -S--------  ----------  ----------  ----------
corl.4    ----------  -S--------  ----------  ----------  ----------
6'dcs     ----------  GS-QA----L  K--IH---VS  -QD-V-----  --VTEN-PHcorl.1    VLPALQNSLR  NLKLDYLDLY  LIHHPVSLKP  GKFVNEIPKD  HILPMDYKSV
corl.2    ----------  ----E-----  ----------  --L-------  ----------
corl.3    ----------  ----------  ----------  ----------  ----------
corl.4    ----------  ----E-----  ----------  ----------  ----------
6'dcs     -----RK--K  T-Q-E-----  ---W-L-SQ-  ---SFP-EVE  DL--F-V-G- corl.1    WAAMEECQTL  GFTRAIGVCN  FSCKRLQELM  ETANSPPVVN  QVEMSPTLHQ
corl.2    ----------  --------S-  ----K-----  A--KI-----  ----------
corl.3    ----------  ----------  ----K-----  AA-KI-----  ----------
corl.4    ----------  --------S-  ----K-----  AA-KI-----  ----------
6'dcs     -ES-----K-  -L-K----S-  --V-K--N-L  SV-TIR---D  ----NLAWQcorl.1    KNLREYCKAN  NIMITAHSVL  GAVGAAWGTN  AVMHSKVLHQ  IAVARGKSVA
corl.2    ----------  ----------  --I--P--S-  ---D------  ----------
corl.3    ----------  ----------  --IC-P--S-  ---D------  ----------
corl.4    ----------  ----------  --I--P--S-  ---D------  ----------
6'dcs     -K---F--E-  G-IV--F-P-  RK--SR-P-   E--END--KE  --E-H---I- corl.1    QVSMRWVYQQ  GASLVVKSFN  EARMKENLKI  FDWELTAEDM  EKISEIPQSR
corl.2    ----------  ----------  ----------  --S-------  ----------
corl.3    ----------  ----------  -G--------  --------N-  ----------
corl.4    ----------  ----------  -G--------  ----------  ----------
6'dcs     ---L--L-E-  -VTF-P--YD  KE--NQ--H-  ---A--EQ-H  H---Q-S--- corl.1    TSSAAFLLSP  TGPFKTEEEF  WDEKD
corl.2    ----D-----  ----------  -----
corl.3    ----D-----  ----------  -----
corl.4    ----------  ----------  -----
6'dcs     .....LISG-  -K-..QLADL  --DQI
```

FIGURE 8
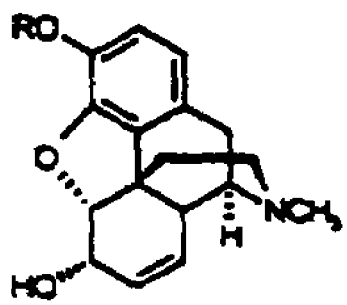
| Substrate | R | $K_m$ |
|---|---|---|
| Codeine | CH₃ | 157 μM |
| Morphine | H | 200 μM |
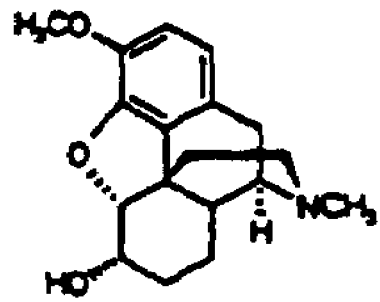
| Substrate | $K_m$ |
|---|---|
| Dihydrocodeine | 628 μM |
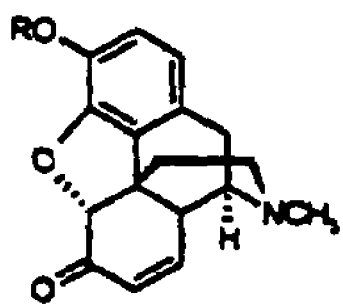
| Substrate | R | $K_m$ |
|---|---|---|
| Codeinone | CH₃ | 48 μM |
| Morphinone | H | 143 μM |
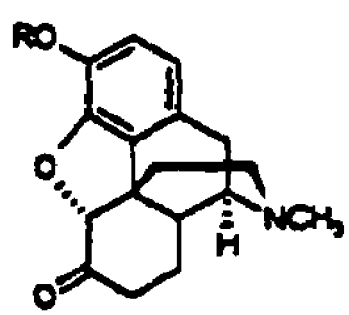
| Substrate | R | $K_m$ |
|---|---|---|
| Hydrocodone | CH₃ | 55 μM |
| Hydromorphone | H | 90 μM | corl.1
cds6-971

Fig 10

```
GAAAAATGGAGAGTAATGGTGTACCTATGATCACTCTCAGTTCCGGCATTCGGATGCCTGCTTTAGGTATGGGAA
CAGCTGAAACAATGGTAAAAGGAACAGAAAGAGAGAAATTGGCGTTTTTGAAAGCGATAGAGGTCGGTTACAGAC
ACTTCGATACAGCTGCTGCATACCAAACTGAAGAGTGTCTTGGTGAAGCTATAGCTGAAGCACTTCAACTTGGTC
TAATAAAATCTCGAGATGAACTCTTCATCACTTCCAAGCTCTGGTGCGCTGATGCTCACGCTGATCTTGTCCTCC
CTGCTCTTCAGAATTCTCTGAGGAATCTTAAAATTGGACTATCTTGATCTATATTTGATACACCATCCGGTAAGCT
TGAAGCCAGGGAAGTTTGTTAACGAAATACCAAAGGATCATATCCTTCCAATGGACTACAAATCTGTATGGGCAG
CCATGGAAGAGTGTCAGACCCTTGGCTTCACTAGGGCAATCGGGTCTGTAAATTTCTCATGCAAAAAGGCTTCAAG
AGTTGATGGAAACAGCCAACAGCCCTCCAGTTGTGAATCAAGTGGAGATGAGCCCGACTTTACATCAAAAAAATC
TGAGGGAATATTGCAAGGCCAATAATATCATGATCACCGCACACTCAGTTTTGGGAGCCGTAGGTGCCGCCTGGG
GCACCAATGCAGTTATGCATTCTAAGGTGCTTCACCAGATTGCTGTGGCCAGAGGAAAATCTGTTGCCCAGGTTA
GTATGAGATGGGTTTACCAGCAAGGCGCGAGTCTTGTGGTGAAAAGTTTCAATGAAGCGAGGATGAAGGAAAACC
TTAAGATATTTGATTGGGAACTAACGGCAGAAGACATGGAAAAGATCAGTGAGATTCCACAATCTAGAACAAGCT
CTGCTGCTTTCTTGTTATCACCGACTGGACCTTTCAAAACTGAAGAAGAGTTCTGGGATGAGAAGGATTGAAACA
TCAATTATAGATGGTAAGTGAGGACTGTCAAAAAAGTAATCAGTTTTTCCCTCCGTTTTG
``` corl.2
cds 1-966

Fig 11

```
ATGGAGAGTAATGGTGTACCTATGATCACTCTCAGTTCCGGCATTCGGATGCCTGCTTTAGGTATGGGAACAGTT
GAAACAATGGAAAAGGGAACAGAAAGAGAGAAATTGGCGTTTTTGAATGCGATAGAGGTCGGTTACAGACACTTC
GATACAGCTGCTGCATACCAAAGTGAAGAGTGTCTTGGTGAAGCTATAGCTGAAGCACTTCAACTTGGTTTAATA
AAATCTCGAGATGAACTCTTCATCACTTCCAAGCTCTGGTGCGCTGATGCTCACGCTGATCTTGTCCTCCCTGCT
CTTCAGAATTCTCTGAGGAATCTCAAATTGGAGTACCTTGATCTATATTTGATACACCATCCGGTAAGCTTGAAG
CCAGGGAAGCTTGTTAACGAAATACCAAAGGATCATATTCTTCCAATGGACTACAAATCTGTATGGGCAGCCATG
GAAGAGTGTCAGACCCTTGGCTTCACTAGGGCAATCGGTGTCAGTAATTTCTCATGCAAAAAGCTTCAAGAGTTG
ATGGCAACAGCCAAGATCCCTCCAGTTGTCAATCAAGTGGAGATGAGCCCGACTTTACATCAAAAAAATCTGAGG
GAATATTGCAAGGCCAATAATATCATGATCACTGCACACTCGGTTTTGGGAGCCATAGGTGCTCCATGGGGCAGC
AACGCAGTTATGGATTCTAAGGTGCTTCACCAGATTGCTGTGGCAAGAGGAAAATCTGTTGCCCAGGTTAGTATG
AGATGGGTTTACCAGCAAGGCGCGAGTCTTGTGGTGAAAAGTTTCAATGAAGCGAGGATGAAGGAAAACCTTAAG
ATATTTGATTCGGAACTAACGGCAGAAGATATGGAAAAGATCAGTGAGATTCCGCAATCTAGAACAAGCTCTGCT
GATTTCTTGTTATCACCGACTGGACCTTTCAAAACTGAAGAAGAGTTCTGGGATGAGAAGGATTGA
``` corl.3
cds1-966

Fig 12

```
ATGGAGAGTAATGGTGTACCTATGATCACTCTCAGTTCCGGCATTCGGATGCCTGCTTTAGGTATGGGAACAGCT
GAAACAATGGTAAAAGGAACAGAAAGAGAGAAATTGGCGTTTTTGAAAGCGATAGAGGTCGGTTACAGACACTTC
GATACAGCTGCTGCATACCAAAGTGAAGAGTGTCTTGGTGAAGCTATAGCTGAAGCACTTCAACTTGGTCTAATA
AAATCTCGAGATGAACTCTTCATCACTTCCAAGCTCTGGTGCGCTGATGCTCACGCTGATCTTGTCCTCCCTGCT
CTTCAGAATTCTCTGAGGAATCTTAAATTGGACTATCTTGATCTATATTTGATACACCATCCGGTAAGCTTGAAG
CCAGGGAAGTTTGTTAACGAAATACCAAAGGATCATATCCTTCCAATGGACTACAAATCTGTATGGGCAGCCATG
GAAGAGTGTCAGACCCTTGGCTTCACTAGGGCAATCGGGGTCTGTAAATTTCTCATGCAAAAAGCTTCAAGAGTTG
ATGGCAGCAGCCAAGATCCCTCCAGTTGTGAATCAAGTGGAGATGAGCCCGACTTTACATCAAAAAAATCTGAGG
GAATATTGCAAGGCCAATAATATCATGATCACTGCACACTCGGTTTTGGGAGCCATATGTGCTCCATGGGGCAGC
AATGCAGTTATGGATTCTAAGGTGCTTCACCAGATTGCTGTGGCAAGAGGAAAATCTGTTGCCCAGGTTAGTATG
AGATGGGTTTACCAGCAAGGCGCGAGTCTAGTGGTGAAAAGTTTCAATGAAGGGAGGATGAAGGAAAACCTTAAG
ATATTTGATTGGGAACTAACGGCAGAGAATATGGAAAAGATCAGTGAGATTCCGCAATCTAGAACAAGCTCTGCT
GATTTCTTGTTATCACCGACTGGACCTTTCAAAACTGAAGAAGAGTTCTGGGATGAGAAGGATTGA
``` corl.4
cds1-966

Fig 13-1

```
ATGGAGAGTAATGGTGTACCTATGATCACTCTCAGTTCCGGCATTCGGATGCCTGCTTTAGGTATGGGAACAGCT
GAAACAATGGTAAAAGGAACAGAAAGAGAGAAATTGGCGTTTTTGAAAGCGATAGAGGTCGGTTACAGACACTTC
GATACAGCTGCTGCATACCAAAGTGAAGAGTGTCTTGGTGAAGCTATAGCTGAAGCACTTCAACTTGGTTTAATA
AAATCTCGAGATGAACTCTTCATCACTTCCAAGCTCTGGTGCGCTGATGCTCACGCTGATCTTGTCCTCCCTGCT
```

Fig 13-2

CTTCAGAATTCTCTGAGGAATCTCAAATTGGAGTATCTTGATCTATATTTGATACACCATCCGGTAAGCTTGAAG
CCAGGGAAATTTGTTAACGAAATACCAAAGGATCATATTCTTCCAATGGACTACAAATCTGTATGGGCAGCCATG
GAAGAGTGTCAGACCCTTGGCTTCACTAGGGCAATCGGTGTCAGTAATTTCTCATGCAAAAAGCTTCAAGAGTTG
ATGGCAGCAGCCAAGATCCCTCCAGTTGTGAATCAAGTGGAGATGAGCCCTACTTTACATCAAAAAAATCTGAGG
GAATATTGCAAGGCCAATAATATCATGATCACTGCACACTCGGTTTTGGGAGCCATAGGTGCTCCATGGGGCAGC
AATGCAGTTATGGATTCTAAGGTGCTTCACCAGATTGCTGTGGCAAGAGGAAAATCTGTTGCCCAGGTTAGTATG
AGATGGGTTTACCAGCAAGGCGCGAGTCTTGTGGTGAAAAGTTTCAATGAAGGGAGGATGAAGGAAAACCTTAAG
ATATTTGATTGGGAACTAACGGCAGAAGATATGGAAAAGATCAGTGAGATTCCGCAATCTAGAACAAGCTCTGCT
GCTTTCTTGTTATCACCGACTGGACCTTTCAAAACTGAAGAAGAGTTCTGGGATGAGAAGGATTCA cor1.5
partial seq
Fig 14

TGTGGTGAATCAGGTGGAGATGTGGCCGACTTTACATCAAAAAAATCTGAGGGAATATTGCAAGGCCAATAATAT
CATGATCACTGCACACTCGGTTTTGGGAGCCATAGGTGCTCCATGGGGCAGCAATGCAGTTATGGATTCTAAGGT
GCTT cor1.6
partial seq
Fig 15

CTCTGGTGCGCTGATGCTCACGCTGATCTTGTCCTCCCTGCTCTTCAGAATTCTCTGAGGAATCTCAAATTGGAC
TACCTTGATCTATATTTGATACACCATCCGGTAAGCTTGAAGCCAGGGAAGCTTGTTAACGAAATACCAAAGGAT
CATATTCTTCCAATGGACTACAAATCTGTATGGGCAGCCATGGAAGAGTGTCAGACCCTTGGCTTCACTAGGGCA
ATCGGTGTCAGTAATTTCTCATGCAAAAAGCTTCAAGAGTTGATGGCAACAGCCAAGATCCCTCCA

CODEINONE REDUCTASE FROM ALKALOID POPPY

TECHNICAL FIELD

The present invention relates to codeinone reductase from alkaloid poppy plants, the polynucleotides encoding the enzyme and to production of alkaloids from transformed poppy plants.

BACKGROUND

The search for useful drugs of defined structure from plants began with the isolation of morphine from dried latex, or opium, of the opium poppy *Papaver somniferum* in 1806 (Sertürner). The narcotic analgesic morphine and the antitussive and narcotic analgesic codeine, the antitussive and apoptosis inducer noscapine (Ye et al., 1998), and the vasodilator papaverine are currently the most important physiologically active alkaloids from opium poppy. Of these four alkaloids, only papaverine is prepared by total chemical synthesis for commercial purposes. Opium poppy, therefore, serves as one of the most important renewable resources for pharmaceutical alkaloids. Per annum, 90–95% of the approximately 160 tons of morphine that are purified are chemically methylated to codeine, which is then used either directly or is further converted to a variety of derivatives such as dihydrocodeinone and 14-hydroxydihydrocodeinone that find use as antitussives and analgesics (Kutchan, 1998). The illicit production of morphine for acetylation to heroin is unfortunately almost ten times that amount, more than 1200 tons per year (Zenk, 1994).

The enzymatic synthesis of morphine in opium poppy has been almost completely elucidated by M. H. Zenk and coworkers and is summarized by Kutchan (1998). Opium poppy produces more than 100 different alkaloids that are derived from the amino acid L-tyrosine and have the tetrahydrobenzylisoquinoline alkaloid, (S)-reticuline, as a common intermediate. There are three NADPH-dependent reductases involved in the conversion of (S)-reticuline to morphine. (S)-Reticuline must first be converted to (R)-reticuline before the phenanthrene ring with the correct stereochemistry at C-13 can be formed. The inversion of stereochemistry at C-1 of (S)-reticuline occurs by oxidation to the 1.2-dehydroreticulinium ion followed by stereospecific reduction to the R-epimer by 1.2-dehydroreticulinium ion reductase [EC 1.5.1.27] (De-Eknamkul and Zenk, 1992). The second reduction occurs after formation of the phenanthrine nucleus with stereo specific reduction of salutaridine to salutaridinol by salutaridine reductase [EC 1.1.1.248] (Gerardy and Zenk, 1993). The third reduction is the penultimate step in the biosynthetic pathway to morphine, the reduction of codeinone to codeine by codeinone reductase [EC 1.1.1.2471] (FIG. 1; Lenz and Zenk, 1995a,b). The substrate for codeinone reductase, codeinone, exists in an equilibrium with its positional isomer neopinone. In vitro, as codeinone is reduced, this equilibrium is continually driven from neopinone towards codeinone until the substrates are depleted (Gollwitzer et al., 1993). Each of the known enzymes of morphine biosynthesis has been detected in both *P. somniferum* plants and cell suspension culture, yet plant cell cultures have never been shown to accumulate morphine (Kutchan, 1998). Sequences of genes encoding cytochrome P450 reductases have been published in PCT/AU98/000705 which is hereby incorporated by reference.

To date, no other genes specific to morphine biosynthesis in opium poppy have been isolated. Tyrosine/dopa decarboxylase has been investigated at the molecular genetic level, but is involved in multiple biochemical processes in this plant (Facchini and De Luca, 1994). Morphine, along with the chemotherapeutic agents vincristine, vinblastine and camptothecin, is one of the most important alkaloids commercially isolated from medicinal plants. Isolation of the genes of morphine biosynthesis would facilitate metabolic engineering of opium poppy to produce plants with specific patterns of alkaloids and could ultimately lead to an understanding of the inability of plant cell cultures to accumulate morphine.

It is an object of the present invention to overcome or ameliorate at least one of the disadvantages of the prior art, or to provide a useful alternative.

SUMMARY OF THE INVENTION

The narcotic analgesic morphine is the major alkaloid of the opium poppy *Papaver somniferum*. Its biosynthetic precursor codeine is currently the most widely used and effective antitussive agent. Along the morphine biosynthetic pathway in opium poppy, codeinone reductase catalyzes the NADPH-dependent reduction of codeinone to codeine. At least 10 codeinone reductase alleles are present in the genome of the poppy *Papaver somniferum*. Isolation, characterization and functional expression of four of the 10 genes encoding codeinone reductase as described herewith enables methods for controlling alkaloid production in opium poppy plants and cultures by providing a target for genetic manipulation.

Thus, according to a first aspect, there is provided an isolated and purified polynucleotide or a variant, fragment or analog thereof, encoding a codeinone reductase enzyme from an alkaloid poppy plant.

The polynucleotide may be selected from the group consisting of genomic DNA (gDNA), cDNA, or synthetic DNA. Preferred polynucleotides are selected from (a) the polynucleotide sequences shown in FIGS. 10 to 15; (b) the polynucleotide sequences which hybridize under stringent conditions to the complementary sequences of (a); and (c) polynucleotide sequences which are degenerate to polynucleotide sequences of (a) or (b). It will be understood however that the sequences may be expressed in the absence of the native leader sequences or any of the 5' or 3' untranslated regions of the polynucleotide. Such regions of the polynucleotide may be replaced with exogenous control/regulatory sequences in order to optimise/enhance expression of the sequence in an expression system.

The preferred alkaloid-producing poppy plant is *Papaver somniferum*.

It will also be understood that analogues and variants of the polynucleotide encoding a codeinone reductase from alkaloid poppy plants fall within the scope of the present invention. Such variants will still encode an enzyme with codeinone reductase properties and may include codon substitutions or modifications which do not alter the amino acid encoded by the codon but which enable efficient expression of the polynucleotide encoding codeinone reductase enzyme in a chosen expression system. Other variants may be naturally occurring, for example allelic variants or isoforms.

According to a second aspect there is provided an isolated and purified polynucleotide, or a variant, analog or fragment thereof, which codes for prokaryotic or eukaryotic expression of a codeinone reductase enzyme from an alkaloid poppy plant, wherein the polynucleotide is expressed in an environment selected from the group consisting of the extracellular environment, an intracellular membranous compartment, intracellular cytoplasmic compartment or combinations thereof.

The polynucleotide encoding a codeinone reductase may be coupled to another nucleotide sequence which would assist in directing the expression of the reductase with respect to a particular cellular compartment or the extracellular environment.

According to a third aspect there is provided an isolated and purified polynucleotide which is complementary to all or part of the sequence of a polypeptide according to the first aspect.

Such complementary polynucleotides are useful in the present invention as probes and primers, as antisense agents or may be used in the design of other suppressive agents such as ribozymes and the like.

According to a fourth aspect there is provided a recombinant DNA construct comprising the polynucleotide according to any one of the first to third aspects.

Preferably the recombinant DNA construct is a viral or plasmid vector. Such a vector may direct prokaryotic or eukaryotic expression of the polynucleotide encoding a codeinone reductase or it may prevent or reduce its expression. The vector may also be selected from pCAL-c, pGEM-T or pFastBac1. Preferably the promoter used to control expression of the codeinone reductase gene is selected from nos, cauliflower mosaic virus or subterranean clover mosaic virus.

According to a fifth aspect there is provided an isolated and purified codeinone reductase enzyme, being a product of prokaryotic or eukaryotic expression of the polynucleotide of any one of first to third aspects or a DNA construct of the fourth aspect.

The codeinone reductase may be expressed in and by a variety of eukaryotic and prokaryotic cells and organisms, including bacteria, yeasts, insect cells, mammalian and other vertebrate cells, or plant cells. Preferably the expression system is a plant expression system and even more preferred is an alkaloid poppy plant. A suitable alkaloid poppy plant is *Papaver somniferum*.

Variants of the codeinone reductase enzyme which incorporate amino acid deletions, substitutions, additions or combinations thereof, are also contemplated. The variants can be advantageously prepared by introducing appropriate codon mutations, deletions, insertions or combinations thereof, into the polynucleotide encoding the codeinone reductase enzyme. Such variants will retain the properties of the codeinone reductase enzyme, either in vivo or in vitro, and may have improved properties. Other valiants may be naturally occurring, for example allelic variants or isoforms.

For expression of codeinone reductase activity, a fragment of the polynucleotide encoding a codeinone reductase may be employed, such fragment encoding functionally relevant regions, motifs or domains of the reductase protein. Similarly, fragments of the codeinone reductase enzyme resulting from the recombinant expression of the polynucleotide may be used. Functionally important domains of codeinone reductase may be represented by individual exons or may be identified as being highly conserved regions of the protein molecule. Those parts of the codeinone reductase which are not highly conserved may have important functional properties in a particular expression system.

According to a sixth aspect there is provided a cell transformed or transfected with a polynucleotide according to any one of the first to third aspects or a DNA construct according to the fourth aspect.

Cells which may be transfected or transformed with a polynucleotide encoding a codeinone reductase are bacterial, yeast, animal or plant cells. For preference the cells are plant cells. Even more preferred are cells from an alkaloid poppy plant, such as *Papaver somniferum*.

According to the seventh aspect, there is provided a callus transformed or transfected with a polynucleotide according to any one of the first to third aspects or a DNA construct according to the fourth aspect.

According to the eighth aspect, there is provided a plant transformed or transfected with a polynucleotide according to any one of the first or third aspects or a DNA construct according to the fourth aspect wherein the plant exhibits altered expression of the codeinone reductase enzyme. For preference, the altered expression manifests itself in overexpression of the codeinone reductase enzyme. However, reduced expression of codeinone reductase can also be achieved if the plant is transformed or transfected with a polynucleotide which is complementary to the polynucleotide encoding the reductase.

Even more preferably, the transformed or transfected plant is an alkaloid poppy plant, wherein the plant has a higher or different alkaloid content when compared to a plant which has not been so transformed or transfected.

Preferably the transformed or transfected plants having higher or different alkaloid content are *Papaver somniferum*.

According to the ninth aspect, there is provided a method for preparing plants which overexpress a codeinone reductase enzyme, comprising transfecting or transforming a plant cell, a plant part or a plant, with the polynucleotide according to any one of the first to third aspects or a DNA construct according to the fourth aspect.

Preferably the plant overexpressing codeinone reductase is an alkaloid poppy plant and most preferably the poppy plant is *Papaver somniferum*. Suitable promoters to control the expression of the codeinone reductase gene may be derived from for example nos, cauliflower mosaic virus or subterranean clover mosaic virus. Other virus promoters may also be suitable. Further, the use of the endogenous promoter may also be appropriate in certain circumstances. Such a promoter may be co-isolated with the gDNA encoding the codeinone reductase enzyme.

According to the tenth aspect, there is provided a method of altering the yield or type of alkaloid in a plant comprising transforming or transfecting a plant cell, a plant part or a plant with a polynucleotide, or a variant, analog or fragment thereof, encoding a codeinone reductase enzyme, or with a polynucleotide which binds under stringent conditions to the polynucleotide encoding the enzyme.

According to the eleventh aspect, there is provided a method of increasing the yield of alkaloid in a plant comprising transforming or transfecting a plant cell, a plant part or a plant with a polynucleotide, or a variant, analog or fragment thereof, encoding a codeinone reductase enzyme wherein the enzyme is overexpressed in the plant.

According to the twelfth aspect, there is provided a method of altering type or blend of alkaloid in a plant comprising transforming or transfecting a plant cell, a plant part or a plant with a polynucleotide or a variant, analog or fragment thereof, encoding a codeinone reductase enzyme or with a polynucleotide which binds under stringent conditions to the polynucleotide encoding said enzyme.

According to the thirteenth aspect, there is provided a stand of stably reproducing alkaloid poppies transformed or transfected with a polynucleotide according to any one of the first to third aspects or a DNA construct according to the fourth aspect, having altered expression of the codeinone reductase enzyme.

According to the fourteenth aspect, there is provided a stand of stably reproducing alkaloid poppies transformed or transfected with a polynucleotide according to any one of the first to third aspects or a DNA construct according to the fourth aspect, having a higher or different alkaloid content when compared to a plant which has not been so transformed or transfected.

Preferably the stably reproducing alkaloid poppy is *Papaver somniferum*.

According to the fifteenth aspect, there is provided straw of stably reproducing poppies according to the fourteenth aspect having a higher or different alkaloid content when compared to the straw obtained from an alkaloid poppy which has not been transformed or transfected.

According to the sixteenth aspect, there is provided a concentrate of straw according to the fifteenth aspect having a higher or different alkaloid content when compared to the concentrate of straw obtained from an alkaloid poppy which has not been transformed or transfected.

According to the seventeenth aspect, there is provided an alkaloid when isolated from the straw according to the fifteenth aspect or the concentrate according to the sixteenth aspect. Preferably the alkaloid is selected from the group consisting of morphine, codeine, oripavine and thebaine.

According to the eighteenth aspect, there is provided a method for production of poppy plant alkaloids comprising the steps of;

a) harvesting capsules of an alkaloid poppy plant transformed or transfected with a polynucleotide according to any one of the first to third aspects, or a DNA construct according to the fourth aspect, to produce a straw where the poppy plant is such a plant that the straw has a higher or different alkaloid content when compared to the straw obtained from a poppy plant which has not been transformed or transfected; and b) chemically extracting the alkaloids from the straw.

According to the nineteenth aspect, there is provided a method for the production of poppy alkaloids comprising the steps of;

a) collecting and drying the latex of the immature capsules of an alkaloid poppy plant transformed or transfected with a polynucleotide according to any one of the first to fourth aspects, to produce opium wherein the poppy plant is such a plant that the opium has a higher of different alkaloid content when compared to the opium obtained from a poppy plant which has not been transformed or transfected; and b) chemically extracting the alkaloids from the opium.

For preference the alkaloid is morphine, codeine, oripavine or thebaine, but it will be understood that other intermediates in the alkaloid metabolic pathway are also within the scope of the present invention, as are mixtures of alkaloids.

According to a twentieth aspect, the invention provides the polynucleotide sequence encoding codeinone reductase comprised in microbial deposit No. 12737.

According to a twenty-first aspect, the invention provides the polynucleotide sequence encoding codeinone reductase comprised in microbial deposit No. 12738.

According to a twenty-second aspect, the invention provides the polynucleotide sequence encoding codeinone reductase comprised in microbial deposit No. 12739.

According to a twenty-third aspect, the invention provides the polynucleotide sequence encoding codeinone reductase comprised in microbial deposit No. 12740.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The reduction of codeinone to codeine by codeinone reductase drives the non-enzymatic equilibrium between neopinone and codeinone in a physiologically forward direction. The demethylation of thebaine and codeine are each thought to be catalyzed by cytochrome P450-dependent enzymes.

FIG. 2. Partial amino acid sequences of native codeinone reductase. Peptide 3 is SEQ ID NO: 9, Peptide 7 is SEQ ID NO: 10, Peptide 14 is SEQ ID NO: 11, Peptide 16 is SEQ ID NO: 12, Peptide 17 is SEQ ID NO: 13, Peptide 25 is SEQ ID NO: 14, and Peptide 29 is SEQ ID NO: 15.

Codeinone reductase was purified to apparent electrophoretic homogeneity from cell suspension cultures of opium poppy and hydrolyzed with endoproteinase Lys-C. The resultant peptide mixture was resolved by HPLC and the amino acid sequences of seven peptides were obtained.

FIG. 3. Amino acid sequence homology of codeinone reductase internal peptides.

Codeinone reductase peptides 3, 7, 14, 16, and 17 aligned with the reductase subunit of the 6'-deoxychalcone synthase complex from alfalfa (SEQ ID NO: 16), glycyrrhiza (SEQ ID NO: 17) and soybean (SEQ ID NO: 18) allowing the relative positioning of these internal peptides from opium poppy (SEQ ID NO: 19).

FIG. 4. Amino acid sequence comparison of codeinone reductase isoforms.

The amino acid sequences derived from translation of the nucleotide sequences of cor1.1–1.4 (SEQ ID NOS. 26, 27, 28, and 29, respectively) as compared to the reductase subunit of the 6'-deoxychalcone synthase complex from soybean (SEQ ID NO: 18) indicate the very high sequence identity between isoforms (95–96%) and this reductase of phenylpropanoid metabolism (53%). The complete amino acid sequence of cor1.1 (SEQ ID NO: 26) is shown, but only those non-identical residues of the four subsequent sequences.

Figure 5:
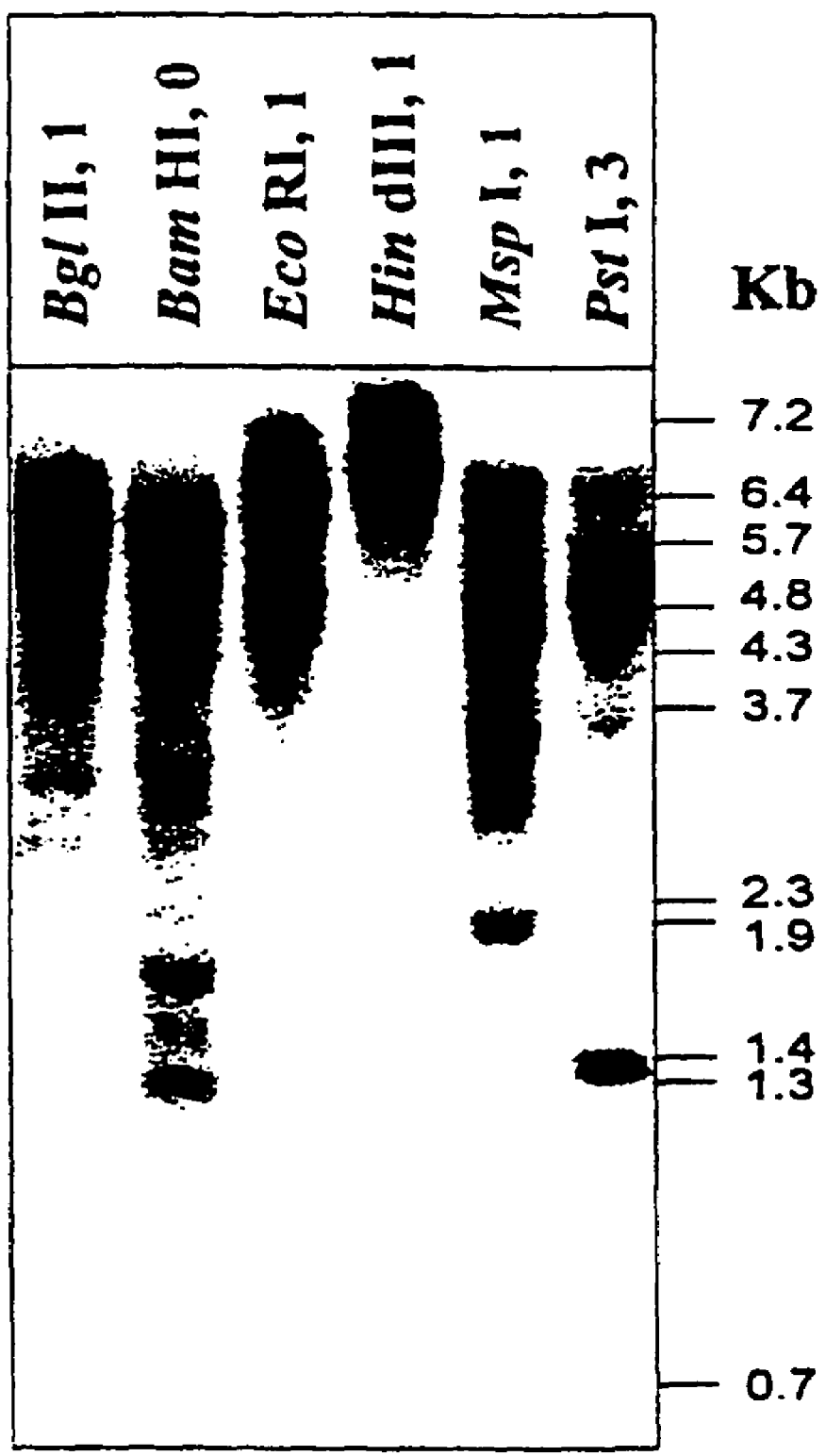

FIG. 5. Genomic DNA gel blot analysis of the codeinone reductase gene family in opium poppy.

Genomic DNA isolated from opium poppy cell suspension cultures was hybridized to cor1.1 full-length cDNA and was visualized by phosphorimaging. The numbers following the restriction enzyme names indicate the number of recognition sites that occur within the cor1.1 reading frame. This high stringency Southern analysis indicates the presence of at least ten alleles in the opium poppy genome.

Figure 6:
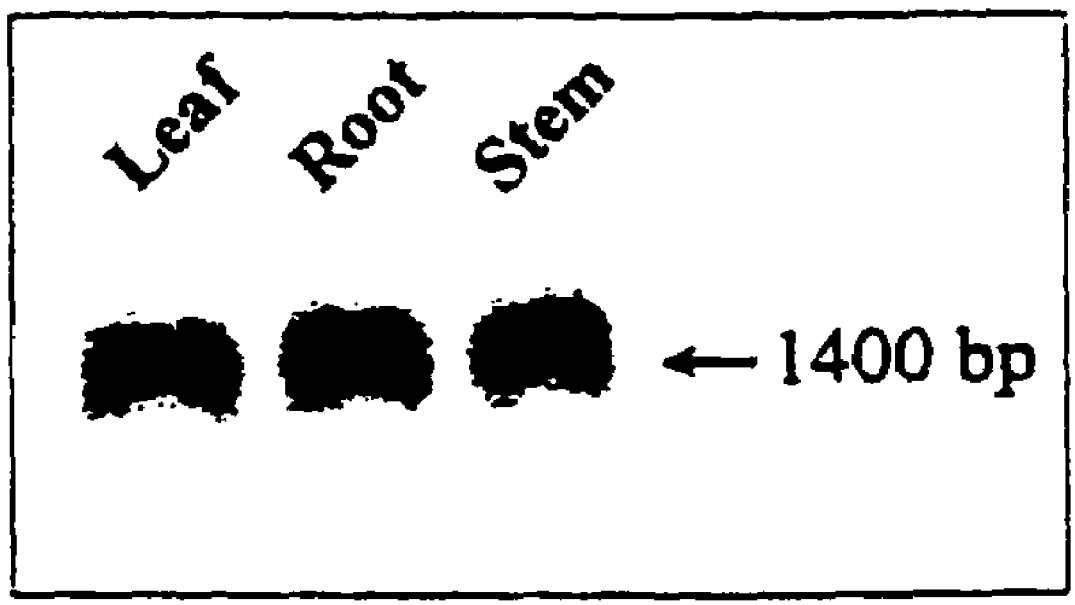

FIG. 6. RNA gel blot analysis of distribution of codeinone reductase transcript in a mature opium poppy.

The gel blot was prepared from RNA isolated from leaf mid rib, lateral root and 12 cm of stem tissue directly beneath the receptacle of an opium poppy plant 2 days after petal fall. 50 µg of total RNA were loaded per gel lane. The RNA was hybridized to cor1.1 full length cDNA and was visualized by phosphorimagery.

Figure 7:
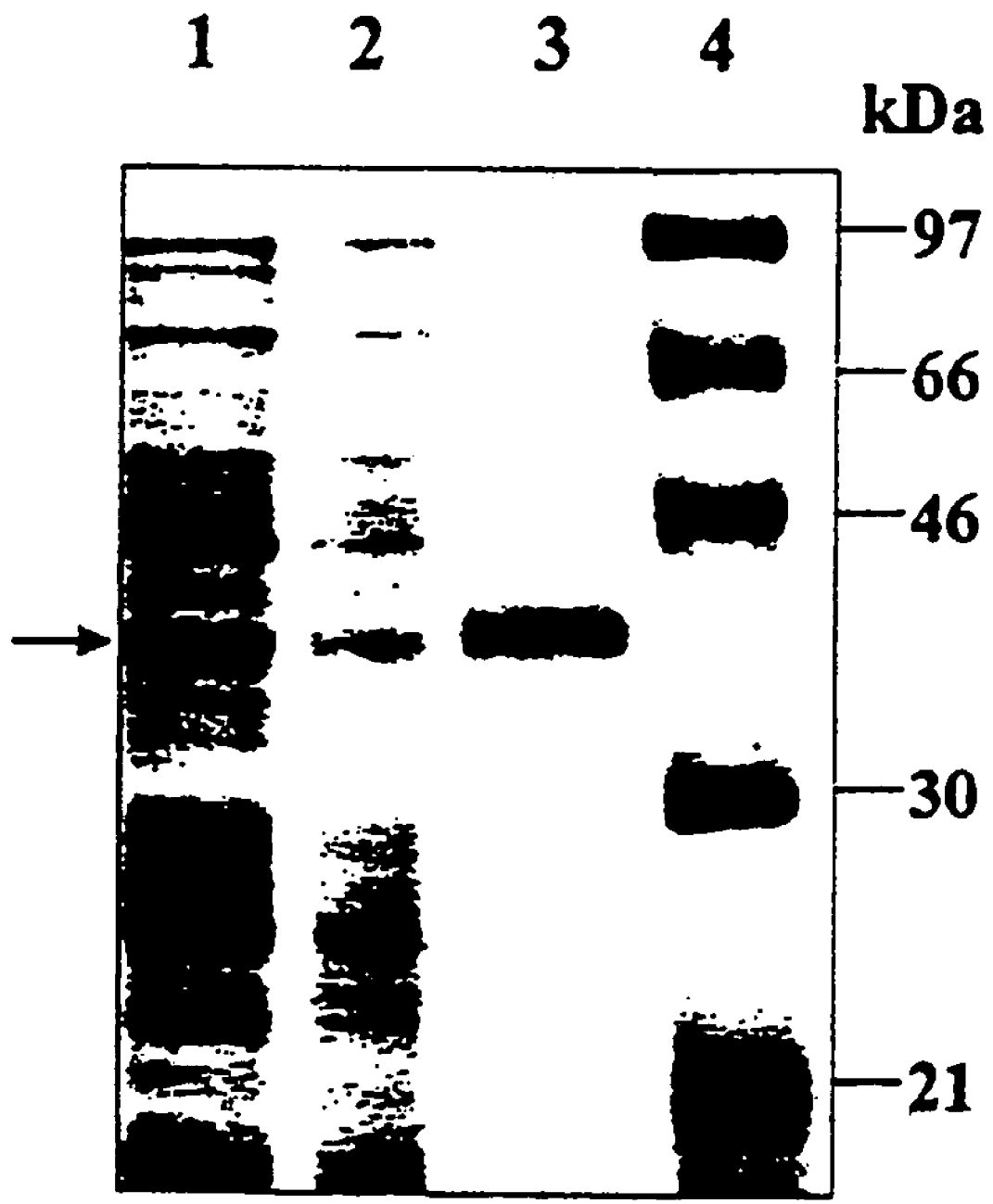

FIG. 7. SDS-PAGE analysis of fractions from the purification of codeinone reductase fusion protein from *E. coli*.

Codeinone reductase was expressed as a C-terminal fusion with a 25 amino acid calmodulin-binding peptide in E. coli BL21 (DE3)pLysS. Protein bands were visualized with coomassie brilliant blue R-250. Lane 1, 15 µg crude protein from an extract of E. coli BL21 (DE3)pLysS containing the codeinone reductase cDNA before IPTG induction; lane 2, 10 µg crude protein from an extract of E. coli BL21 (DE3)pLysS containing the codeinone reductase cDNA 3 h after IPTG induction; lane 3, 5 µg protein from the calmodulin affinity chromatography eluate after concentration using a Centriprep 30 column (Amicon); lane 4, Rainbow Marker protein standards (Amersham). Arrow indicates position of codeinone reductase fusion protein.

FIG. 8. Chemical structures of alkaloids serving as substrates for codeinone reductase.

Of the twenty-six potential substrates tested, only seven were transformed by codeinone reductase. The names of the untransformed compounds are given in the Description of Preferred Embodiments. Codeinone is the physiological substrate for this enzyme in most, if not all, varieties of opium poppy. Morphinone also serves as a physiological substrate in Tasmanian varieties. The $K_m$ values provided for those seven substrates were determined for COR1.3.

Figure 9:
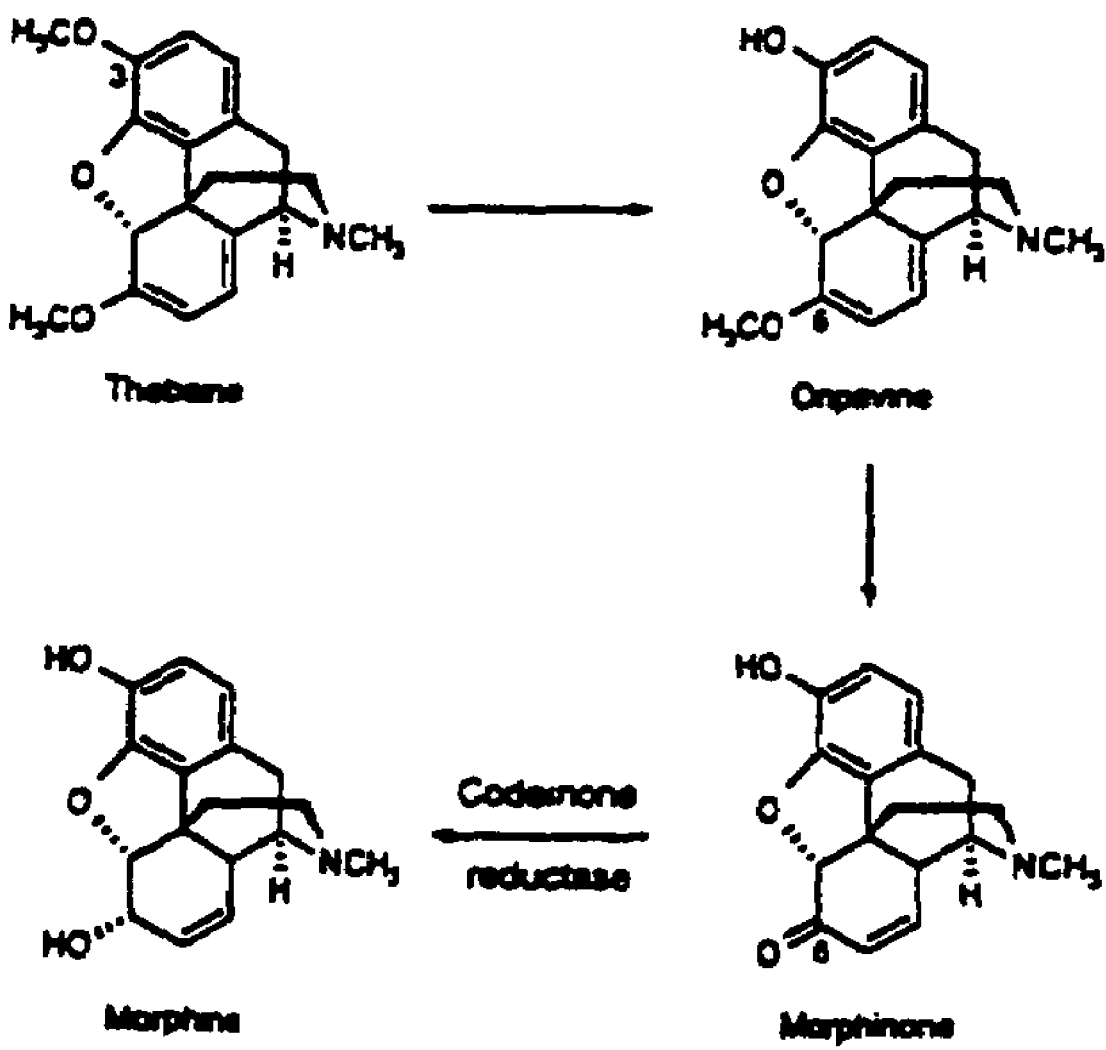

FIG. 9. Proposed alternative biosynthetic pathway leading from thebaine to morphine in opium poppies from Tasmania.

This alternative biosynthetic pathway was proposed after oripavine was discovered in Tasmanian varieties of opium poppy (Brochmann-Hanssen, 1984). Codeinone reductase from non-Tasmanian varieties can also catalyze the reduction of morphinone to morphine (Lenz and Zenk, 1995b). COR1.1–COR1.4 each catalyzed this reduction with equivalent specific activity. The demethylation of thebaine and codeine are thought to be catalyzed by cytochrome P450-dependent enzymes.

FIG. 10. cDNA sequence of cor1.1. (SEQ ID NO: 20)
FIG. 11. cDNA sequence of cor1.2. (SEQ ID NO: 21)
FIG. 12. cDNA sequence of cor1.3. (SEQ ID NO: 22)
FIG. 13. cDNA sequence of cor1.4. (SEQ ID NO: 23)
FIG. 14. Partial cDNA sequence of cor1.5. (SEQ ID NO: 24)
FIG. 15. Partial cDNA sequence of cor1.6. (SEQ ID NO: 25)

DESCRIPTION OF THE PREFERRED EMBODIMENTS cDNas that encode codeinone reductase were isolated. Four full-length reading frames and two partial clones (FIGS. 10 to 15) were isolated that represent six alleles from a gene family that may have at least 10 members. An analysis of RNA and enzyme activity from various stages of developing opium poppy seedlings and roots, stem, leaf and capsule of mature poppy plants indicated that transcript from these alleles is present throughout the plant at all developmental stages, with the highest total enzyme activity being in the capsule after petal fall. This would suggest that morphine biosynthesis occurs in all major plant organs starting within the first seven days after seed germination. Biosynthesis of morphine continues throughout the life cycle of this annual with the highest biosynthetic activity taking place in the capsule after petal fall, consistent with the amount of biosynthetic enzyme present. The amount of extractable RNA remained high in the capsule until three days after petal fall, after which time the quantity of extractable RNA decreased rapidly.

A biochemical analysis of four functionally expressed alleles, cor1.1-cor1.4, revealed no significant differences in the temperature or pH optima, $K_m$ values or substrate specificity of the isoforms. All isoforms were able to reduce morphinone to morphine.

Purification and Amino Acid Sequence Analysis of Opium Poppy Codeinone Reductase Codeinone reductase was purified to apparent electrophoretic homogeneity from opium poppy cell suspension cultures and the amino acid sequence of seven endoproteinase Lys-C-generated peptides was determined (FIG. 2). A comparison of these amino acid sequences with those available in the GenBank/EMBL sequence database allowed a relative positioning of peptides 7, 14 and 16 due to sequence homology with an NADPH-dependent reductase from members of the Fabaceae—alfalfa, glycyrrhiza and soybean (6'-deoxychalcone synthase) that synthesizes 4,2',4'-trihydroxychalcone in co-action with chalcone synthase (FIG. 3) (Welle et al., 1991). PCR primers were then designed based on the codeinone reductase peptide sequences. The sequences of the primers used in the first round of PCR were:

```
SEQ ID NO: 1
5'-GAA CTT TTT ATA ACT TCT AA-3'        (derived
     G   C   C   C   G   C               from Pep-
                 T                        tide 14)
                                          and SEQ ID NO: 2
3'-GTG GTC TAA CGT CAI CGT TCI CCT TT-5' (derived
     A               A G       C         from Pep-
                                          tide 7)
```

Resolution of an aliquot of the first PCR experiment by agarose gel electrophoresis revealed a mixture of DNA products, none of which was the expected band of approximately 480 bp. This was presumably due to the relatively low specificity of the degenerate primers coupled to a low abundance of codeinone reductase transcript. Another aliquot of the first PCR reaction mixture was, therefore, used as template for nested PCR with the following primers:

```
SEQ ID NO: 1
5'-GAA CTT TTT ATA ACT TCT AA-3'        (same as Pep-
     G   C   C   C   G   C               tide 14 primer
                 T                        above) and SEQ ID NO: 3
3'-CAI CAC TTA GTT CAC CTT TAC-5'        (nested primer
     G           C       C               derived from
                                          Peptide 16)
``` to yield an approximately 360 bp DNA fragment and the following primers to yield an approximately 180 bp DNA product:

```
SEQ ID NO: 4
5-'GTI GTI AAC CAA GTI GAA ATG AGI CCI AC-3'  (nested primer derived from
         T   G           G    TC                Peptide 16) and SEQ ID NO: 2
3'-GTG GTC TAA CGT CAI CGT TCI CCT TT-5'      (same as Peptide 7 primer above)
     A               A G       C
```

The results from the nested PCR were bands of the expected size. The translation of the nucleotide sequences of these PCR products indicated that they encode codeinone reductase.

Isolation of cDNAs Encoding Codeinone Reductase

Screening of approximately 200,000 clones of a primary cDNA library prepared from opium poppy RNA isolated from capsule and cell suspension culture did not result in the identification of codeinone reductase clones. Likewise, difficulty was also confronted with detecting a band on RNA gel blots that corresponds to the size expected for codeinone reductase. In order to overcome the apparent problem of low steady state levels of codeinone reductase transcript, RACE-PCR was used to generate both the 5'- and 3'-portions of the cDNA (Frohman, 1993). A series of non-degenerate primers based on the nucleotide sequence information determined for the PCR product generated as described in the previous section were used for 5'- and 3'-RACE. The nucleotide sequence of the resultant 5'- and 3'- partial clones were thus determined in three major fragments and suggested the presence of isoforms. The full length cDNA clones were then generated by RT-PCR using the following primers and RNA isolated from opium poppy cell suspension culture as template:

SEQ ID NO: 5

5'-ATG GAG AGT AAT GGT GTA CCT-3' (located at the 5'-terminus) and

SEQ ID NO: 6

3'-TCT ACC ATT CAC TCC TGA CAG-5' (located in the 3'-flanking region)

followed by nested PCR with the following primer pair:

```
SEQ ID NO: 7
5'-ATG GCT AGC ATG GAG AGT AAT GGT GTA CCT ATG-3' (located at the
         Nhe 1                                    5'-terminus)
and SEQ ID NO: 8
3'-CTT CTC AAG ACC CTA CTC TTC CTA CCT AGG GAA-5' (located at the
                                    Bam HI       3'-terminus).
```

The PCR product was digested with the restriction endonucleases Nhe I/Bam HI, ligated into Nhe I/Bam HI digested pCAL-c and transformed into *Escherichia coli* BL21(DE) pLysS. Each cDNA was hence constructed in frame in front of DNA encoding a 25 amino acid long calmodulin-binding peptide to facilitate eventual heterologous protein purification. Single colonies were grown in 3 ml medium and were assayed for the ability to reduce codeinone. Of forty colonies tested, ten were found to contain functional enzyme. Nucleotide sequence determination of these ten cDNAs resulted in the identification of four alleles encoding codeinone reductase. The analogous PCR products had also been prepared with the cDNAs placed behind the calmodulin-binding peptide gene in pCAL-n-EK, but only the C-terminal fusion proteins bound the calmodulin affinity resin, indicating that the amino terminus of the fusion protein lies within the folded polypeptide.

By sequence comparison, codeinone reductase clearly belongs to the aldo/keto reductase family, a group of structurally and functionally related NADPH-dependent oxidoreductases. Members of this family possess three consensus sequences that are also positionally conserved: aldo/keto reductase consensus 1 (amino terminus)—G (F,Y)R(H,A,L) (L,I,V,M,F)D(S,T,A,G,C)(A,S) X X X X X E X X (L,I,V,M) G [cor1.1—G Y R H F D T A A A Y Q T E E C L G]; aldo/keto reductase consensus 2 (central)—(L,I,V,M,F,Y) X X X X X X X X (K,R,E,Q) X (L,I,V,M) G (L,I,V,M) (S,C) N (F,Y) [cor1.1—M E E C Q T L G F T R A I G V C N F]; aldo/keto reductase consensus 3 (carboxy terminus)—(L,I, V,M) (P,A,I,V)(K,R)(S,T) X X X X R X X (G,S,T,A,E,Q,K) (N,S,L) X X (L,I,V,M,F,A)[cor1.1—V V K S F N E A R M K E N L K I]. This third consensus sequence is centred around a lysine residue, the modification of which has been shown to affect the catalytic efficiency of aldose and aldehyde reductases (Morjana et al., 1989).

The four functional full-length cDNAs (cor1.1, cor1.2, cor1.3 and cor1.4) encoding codeinone reductase share approximately 95–96% sequence identity (FIG. 4). These sequences are comprised in microbial deposit Nos. DSM 12737, DSM 12738, DSM 12739 and DSM 12740 respectively, deposited at Deutsche Sammlung von Mikroorganismen und Zellkulturen GmbH (DSMZ) of Mascheroder Weg 1b, D-38124 Braunschweig, Germany on 16 Mar. 1999. In addition, a similar cDNA generated by PCR (cor2) was 70% identical to the codeinone reductase cDNAs, but was not functional. These opium poppy cDNAs were 53% identical to soybean NADPH-dependent reductase 6'-deoxychalcone synthase (Welle et al., 1991) (FIG. 4), 33% identical to rat 3-hydroxysteroid dehydrogenase [EC 1.1.1.50], 38% identical to bovine prostaglandin F synthase [EC 1.1.1.188], 37% identical to apple D-sorbitol-6-phosphate dehydrogenase [EC1.1.1.200], 38% identical to bacterial (*Pseudomonas putida*) morphine 6-dehydrogenase [EC 1.1.1.218] and 35% identical to yeast (*Pichia stipitis*) xylose reductase (Amore at al., 1991).

Genomic DNA Analysis and Gene Expression Pattern

Genomic DNA was used as template for a PCR analysis of cor1.1–cor1.4. Each gene was found to contain one intron that was conserved in size (443 bp) and location (beginning after nucleotide +561) within the open reading frame, but not in nucleotide sequence. In comparison, cor2 contained two introns beginning after nucleotides +321 and +514. Genomic DNA gel blot analysis using cor1.1 as hybridization probe resulted in a complex hybridization pattern that suggests the presence of at least ten genes that could encode codeinone reductase in opium poppy (FIG. 5). From the isolation and nucleotide sequence analysis of cDNA clones, it is certain that at least six of these ten genes are expressed in the plant and plant cell suspension culture. (Two additional partial cDNAs (cor1.5 and cor1.6; FIGS. 14 and 15) were generated by RT-PCR using plant RNA as template.) When the peptide sequences presented in FIG. 2 are compared with the translations of the cDNA sequences in FIG. 4, it is clear that a mixture of isoforms was purified for amino acid sequence analysis. From the initial biochemical analysis of codeinone reductase, evidence for only two isoforms in the poppy plant and one isoform in poppy cell suspension culture was observed (Lenz and Zenk, 1995b).

RNA gel blot analysis indicated the presence of a very weakly hybridizing RNA of approximately 1.4 kb in poppy leaf, root and stem of a mature plant two days after petal fall (FIG. 6). Since cor1 transcript was apparently present at very low levels, further analysis was undertaken by nested RT-PCR. Morphinan alkaloids begin to accumulate rapidly in poppy seedlings four to seven days after germination (Rush et al., 1985; Wieczorek et al., 1986). An analysis of codeinone reductase enzyme activity and transcript accumulation showed that enzyme activity is at 310 pkat/g dry tissue weight (dwt) already at day seven after germination (Table 1). This activity remains at that level throughout a three week growth period, then decreases to 148 pkat/g dwt by the eighth week. In comparison, opium poppy cell suspension culture also contains 330 pkat/g dwt enzyme activity. Transcript was detected by RT-PCR for cor1.1-cor1.4 at all developmental stages. Since two PCR amplifications were necessary in order to detect cor1 transcript, a comparative quantitation was not undertaken.

The distribution of codeinone reductase enzyme activity and transcript was also investigated in mature opium poppy plants two days after petal fall. On a dry tissue weight basis, most activity was present in the capsule (730 pkat/g dwt), then the lateral root (560 pkat/g dwt) followed by stem and leaf lamina (Table 2). Again, no differences could be found in the distribution pattern of the four isoforms by RT-PCR.

TABLE 1

Analysis of codeinone reductase enzyme activity and transcript in developing opium poppy and in plant suspension culture.

| Plant Material | Plant age (days) | Specific activity (pkat/mg) | Total activity (pkat/dwt) | Transcript detection* |
|---|---|---|---|---|
| 3 cm | 7 | 11 | 310 | + |
| 5 cm | 14 | 9 | 330 | + |
| 7 cm | 21 | 8 | 310 | + |

TABLE 1-continued

Analysis of codeinone reductase enzyme activity and transcript in developing opium poppy and in plant suspension culture.

| Plant Material | Plant age (days) | Specific activity (pkat/mg) | Total activity (pkat/dwt) | Transcript detection* |
|---|---|---|---|---|
| 20 cm | 56 | 12 | 150 | + |
|  | 7 | 10 | 330 | + |

*Presence of transcript in each RNA population was determined by performing two nested PCR amplifications as described in the Examples.

TABLE 2

Analysis of codeinone reductase enzyme activity and transcript in developing opium poppy two days after petal fall.

| Plant Part | Specific activity (pkat/mg) | Total activity (pkat/dwt) | Transcript detection[a] |
|---|---|---|---|
| Capsule | 25 | 730 | + |
| Stem[b] | 30 | 250 | + |
| Leaf lamina | 10 | 120 | + |
| Lateral root | 90 | 560 | + |

[a]Presence of transcript in each RNA population was determined by performing two nested PCR amplifications as described in the Examples.
[b]Stem tissue beginning at the receptacle and extending 12 cm downwards was extracted. Plants were approximately 120 cm high.

Functional Characterization of the Codeinone Reductase Alleles

The four codeinone reductase isoform-calmodulin-binding peptide fusion proteins were purified from *E. coli* lysates in one step with a calmodulin affinity column. Beginning with 250 mg total protein in the bacterial extract, 10.5 mg codeinone reductase with a specific activity of 5.2 nkat/mg protein could be obtained in 73% yield. Aliquots from a typical purification analyzed by SDS-PAGE are shown in FIG. 7. Codeinone reductase purified by this method is nearly homogeneous and demonstrated properties that compared favourably to those of the native enzyme (Lenz and Zenk, 1995b).

The temperature optimum, pH optimum and $K_m$ values for codeinone, codeine, NADPH and NADP were determined for each of the isoforms ($K_m$ values are indicated in Table 3). Significant differences in these values were not found. For all isoforms, the temperature optimum for reduction (physiologically forward reaction) was 28° C., for oxidation (physiologically reverse reaction) was 30° C., the pH optimum for reduction was 6.8 and for oxidation was 9.0. The isoforms were also tested for their ability to transform morphinan alkaloids structurally related to codeinone and codeine. The reductive reaction with NADPH as cofactor functions with morphinone, hydrocodone and hydromorphone as substrate. The oxidative reaction with NADP as cofactor functions with morphine and dihydrocodeine as substrate. The $K_m$ values for, and structures of, these additional substrates with COR1.3 are shown in FIG. 8. In all cases, the physiologically forward reaction yielded lower $K_m$ values than the physiologically reverse reaction, with codeinone having the lowest $K_m$ value at 48 μM. No differences in temperature or pH optimum were observed whether codeinone or morphinone were used as substrate in the assay. NADH could not substitute for NADPH with any of the isoforms. Tritium was enzymatically transferred to codeinone from [4R-$^3$H]NADPH, but not from [4S-$^3$H]NADPH, indicating that codeinone reductase stereospecifically abstracts the pro-R hydrogen from the cofactor.

TABLE 3

Comparison of properties of codeinone reductase isoforms

|  | COR1.1 | COR1.2 | COR1.3 | COR1.4 |
|---|---|---|---|---|
| Amino acid identity (%) | 100 | 95 | 96 | 96 |
| $K_m$ codeinone (μM) | 58 | 62 | 48 | 50 |
| $K_m$ NADPH (μM) | 180 | 220 | 205 | 197 |
| $K_m$ codeine (μM) | 220 | 200 | 187 | 140 |
| $K_m$ NADP (μM) | 53 | 58 | 45 | 55 |
| Calculated $M_r$ | 35,808 | 35,704 | 35,797 | 35,705 |
| Calculated pI | 6.25 | 5.71 | 6.32 | 6.33 |

Figure 1:
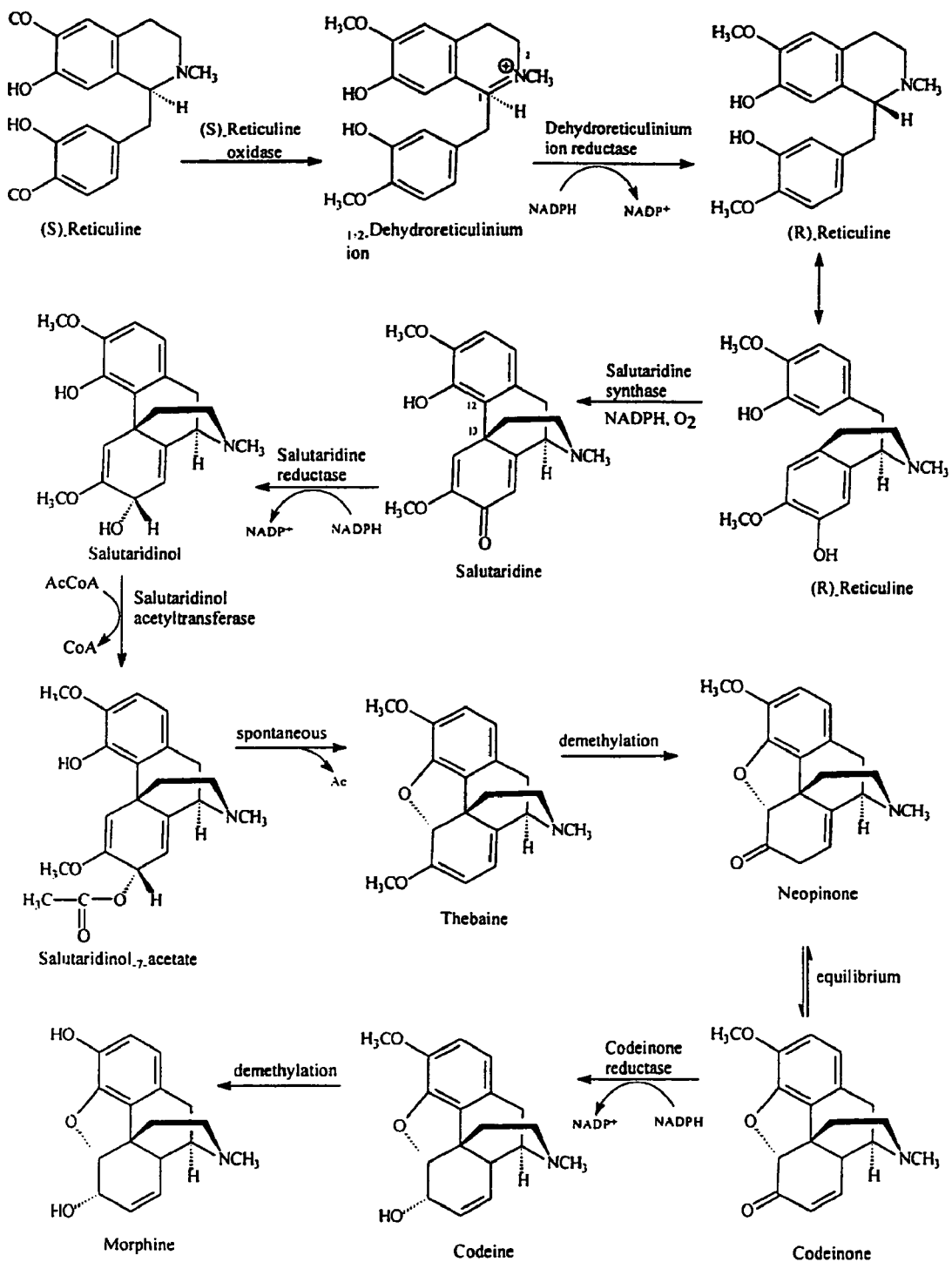
FIG. 1. Biosynthetic pathway leading from S-Reticuline to morphine in the opium poppy, *Papaver somniferum*.

The reduction of codeinone to codeine is the last of three NADPH-dependent reductions that occur along the biosynthetic pathway leading from (S)-reticuline to morphine in opium poppy. The two other potential substrates for reduction, the 1,2-dehydroreticulinium ion and salutaridine (FIG. 1), or for the physiologically reverse reaction, salutaridinol and (R)-reticuline, were tested as substrates; with the codeinone reductase isoforms. None of these alkaloids served as substrate indicating that codeinone reductase can catalyze only one reductive step in morphine biosynthesis. In addition, the following analogs were also inactive: (S) and (R)-norreticuline, (S)-reticuline and norcodeine.

Since codeinone reductase showed sequence similarity to several members of the aldo/keto reductase family, a series of substrates were tested to reflect members from carbohydrate and steroid metabolism. D-Sorbitol-6-phosphate, D-xylose, prostaglandin D1,5-androstene-3β,17β-diol, 5α-androstan-17β-ol-3-one, 5α-cholestane-3β-ol, β-estradiol, cyclohexanone and 2-cyclohexene-1-one were not transformed by codeinone reductase. The highest amino acid sequence identity (53%) was, however, to the reductase subunit of the 6'-deoxychalcone synthase complex from soybean (Welle et al., 1991). In order to test for a functional evolutionary relationship between isoflavonoid and alkaloid anabolism, codeinone reductase was analyzed for the ability to substitute for the reductase in the formation of 6-deoxychalcone in co-action with either native chalcone synthase or native stilbene synthase from *Pinus sylvestris*. In the presence of 4-coumaryl-CoA, malonyl-CoA, NADPH, chalcone synthase and codeinone reductase or cinnamoyl-CoA, malonyl-CoA, NADPH, stilbene synthase and codeinone reductase, formation of product was not observed. Likewise, the reductase of the 6'-deoxychalcone synthase complex could neither reduce codeinone in the presence of NADPH nor oxidize codeine in the presence of NADP.

EXAMPLE 1

Purification of Native Enzyme and Amino Acid Sequence Analysis

Cell suspension cultures of the opium poppy *Papaver somniferum* were routinely grown in either 1-liter conical flasks containing 400 ml of Linsmaier-Skoog medium (Linsmaier and Skoog, 1965) over 7 days at 23° C. on a gyratory shaker (100 rpm) in diffuse light (750 lux). Differentiated opium poppy plants were grown outdoors in Upper Bavaria. Seedlings were grown on substrate from 7 to 56 days in a greenhouse at 20° C., 65% relative humidity and 12 h cycles of light and dark.

A mixture of codeinone reductase isoforms was purified from opium poppy cell suspension cultures exactly according to Lenz and Zenk (1995b). The purified enzyme preparation was subjected to SDS/PAGE to remove traces of impurities and the coomassie brilliant blue R-250-visualized band representing codeinone reductase was digested in situ with endoproteinase Lys-C as reported in (Eckerskorn and Lottspeich, 1989, Dittrich and Kutchan, 1991). The peptide mixture thereby obtained was resolved by reversed phase HPLC [column, Merck Lichrospher RP18; 5 μm (4×125 mm); solvent system, (A) 0.1% trifluoroacetic acid, (B) 0.1% trifluoroacatic: acid/60% acetonitrile; gradient of 1% per min; flow rate of 1 ml/min] with detection at 206 nm. Microsequencing of seven of the peptides thus purified was accomplished with an Applied Biosystems model 470 gas-phase sequencer.

EXAMPLE 2

Generation of Partial and Full-Length cDNAs from Opium Poppy

Partial cDNAs encoding codeinone reductases from opium poppy were produced by PCR using cDNA produced by reverse transcription of total RNA isolated from 3 to 5-day-old suspension cultured cells. DNA amplification using either Taq or Pfu polymerase was performed under the following conditions: 4 min at 94° C., 35 cycles of 94° C., 30 sec: 45° C., 30 sec; 72° C., 1 min. At the end of 35 cycles, the reaction mixtures were incubated for an additional 5 min at 72° C. prior to cooling to 4° C. Reamplification of DNA using nested primers was performed as above, but the primer annealing temperature was raised from 45 to 55° C. The amplified DNA was then resolved by agarose gel electrophoresis, the bands of approximately the correct size were isolated and subcloned into pGEM-T (Promega) prior to nucleotide sequence determination. The specific sequences of the oligodeoxynucleotide primers used are indicated above.

Total RNA was isolated and RNA gels were run and blotted as previously described (Pauli and Kutchan, 1998). Genomic DNA was isolated and DNA gels were run and blotted according to Bracher and Kutchan (1992). cDNA clones were labelled by random-primed labelling with [α-$^{32}$P]dCTP and oligodeoxynucleotides were end-labelled with [γ-$^{32}$P]ATP. Hybridized RNA on Northern blots and DNA on Southern blots were visualised with a Raytest BAS-1500 phosphorimager. The entire nucleotide sequence on both DNA strands of full-length cDNA clones in either pGEM-T or pCAL-c was determined by dideoxy cycle sequencing using internal DNA sequences for the design of deoxyoligonucleotides as sequencing primers.

The sequence information requisite to the generation of full-length cDNAs was derived from the nucleotide sequences of the partial cDNAs generated as described above. The complete nucleotide sequence of one reading frame was determined using codeinone reductase specific oligodeoxynucleotide primers in 5'- and 3'-RACE-PCR experiments with a Marathon™ cDNA amplification kit (Clontech). RACE-PCR was performed using the PCR cycles described above. The amplified DNA was then resolved by agarose gel electrophoresis and the band of the approximate expected size was isolated, subcloned into pGEM-T and sequenced.

Nested primer pairs were then used to generate full-length clones for heterologous expression by RT-PCR using opium poppy cell suspension culture RNA as template. The final primers used in clone amplification contained the restriction endonuclease recognition sites Nhe I and Bam HI that were appropriate for subcloning directly into the pCAL-c (Stratagene) expression vector. The specific sequences of these primers are indicated above. RT-PCR was carried out using the PCR cycles given above. The amplified DNA was then resolved by agarose gel electrophoresis and the band of the correct size (972 bp) was excised and isolated for further subcloning into the expression vector.

EXAMPLE 3

Heterologous Expression and Enzyme Purification

Full-length cDNAs generated by RT-PCR were ligated into p-CAL-c and transformed into the *E. coli* strain BL21 (DE3)pLysS. For enzyme assays, single colonies were picked and grown in 3 ml Luria-Bertani medium containing 100 μg/ml ampicillin at 37° C. to an $OD_{590}$ of 0.8. For protein purification, single colonies were picked and grown in 1 l Luria-Bertani medium containing 100 μg/ml ampicillin at 37° C. to an $OD_{590}$ of 1.8. Cells were collected by centrifugation 5 min at 4,000×g and 4° C. The bacterial pellet was resuspended in either 0.1 M potassium phosphate buffer pH 6.8 for the reduction of codeinone or 0.1 M glycine buffer pH 9 for the oxidation of codeine. The bacterial pellet from a 3 ml culture was resuspended in 0.5 ml buffer and that from a one liter culture in 100 ml buffer. The cells were ruptured by sonication. Cellular debris was removed by centrifugation 5 min at 4,000×g and 4° C. and the supernatant used directly for either affinity chromatography purification using the Affinity™ Protein Expression and Purification System according to the manufacturer's instructions (Stratagene) or for enzyme activity measurements according to Lenz and Zenk (1995b).

EXAMPLE 4

Enzyme Assay and Product Identification

The oxidative and reductive reactions catalyzed by codeinone reductase were assayed according to Lenz and Zenk (1995b). The oxidation of codeine to codeinone by heterologously expressed enzyme in a crude bacterial extract was used for large scale production of enzymic product for structure elucidation by $^1H$ NMR, $^{13}C$ NMR and mass spectrometry. The enzyme assays were extracted twice with two volumes of $CHCl_3$, the combined organic phase was reduced in vacuo and resolved by semipreparative HPLC using the following gradient: [column, Knauer LiChrospher 100 RP18 endcapped; 5 μm (16×250 mm); solvent system, (A) 97.99% (v/v) $H_2O$ 2% $CH_3CN$, 0.01% (v/v) $H_3PO_4$, (B) 1.99% (v/v) $H_2O$, 98% $CH_3CN$, 0.01% $H_3PO_4$; gradient: 0–9 min 0–8% B, 9–24 min 8% B, 24–45 min 8–25% B, 45–75 min 25% B, 75–75.3 min 25–0% B, 75.3–90 min 0% B; flow 4.5 ml/min] with detection at 204 nm using authentic codeine (retention time, 38 min) and codeinone (retention time, 49 min) as reference materials. In this manner, 10 mg codeinone was enzymically produced and purified.

Codeinone—$^1H$ (360 MHz, $CDCl_3$) 1.87 (1H, dd $J_{15a/15e}$ 12.2, $J_{15c/15a}$ 3.1, H-1 Se), 2.08 (1H, ddd, $J_{15a/16a}$ 4.5, $J_{15a/15e}$ 12.2, H-15$_a$) 2.29 (1H, ddd, $J_{15a/16a}$ 12.3, $J_{15e/16a}$ 3.1, $J_{16a/16c}$ 3.1, $J_{16a/16e}$ 11.8, H-16$_a$), 2.35 (1H, dd, $J_{10a/10e}$ 18.5, $J_{9/10a}$ 5.9, H-10$_a$), 2.47 (3H, s, $CH_3N$—), 2.63 (1H, dd, $J_{16a/16c}$ 11.8 $J_{15a/16c}$ 4.5, H-16$_e$), 3.12 (1H, d, $J_{10a/10c}$ 18.5, H-10$_c$), 3.21 (1H, m, H-14), 3.43 (1H, m, H-9), 3.85 (3H, s, $CH_3O$—), 4.71 (1H, s, H-5), 6.09 (1H, dd, $J_{7/8}$ 10.1, $J_{7/14}$ 2.8, H-7), 6.62 (1H, d, $J_{1/2}$ 8.3, H-1), 6.66 (1H, dd, $J_{7/8}$ 10.1, $J_{8/14}$ 1.5, H-8), 6.68 (1H, d, $J_{1/2}$ 8.3, H-2); $^{13}C$ (90.6 MHz, $CDCl_3$) 20.5 (C-10), 33.8 (C-15), 41.3 (C-14), 42.8 (NMe), 43.0 (C-13), 46.8 (C-16), 56.8 (OMe), 59.1 (C-9), 88.0 (C-5), 114.8 (C-2), 119.9 (C-1), 125.7 (C-11), 128.9 (C-12), 132.6 (C-7), 142.6 (C-3), 144.9 (C-4) 148.7 (C-8), 194.4 (C-6); EI-MS (70 eV), m/z 297 (M$^+$, 100%), 282 (8), 268 (9), 254 (8), 238 (9), 229 (23), 214 (17), 188 (15) 165 (11), 152 (13), 139 (16), 128 (22), 115 (41).

EXAMPLE 5

Transformation of Plants with Nucleotide Sequences from Genes Encoding Codeinone Reductase Proteins Plant Materials Two plant lines were used in transformation experiments. These were *Nicotiana tabacum* line Wisconsin38, and *Papaver somniferum* line C048. Preparation of plant materials and tissue culture and transformation conditions were as described in An et. al (1986), Hooykaas and Schilperoort (1992) and PCT Application PCT/AU99/00004, all of which are incorporated herein by reference.

Bacterial Strains and Vectors

The disarmed *Agrobacterium tumefaciens* strain LBA4404 was used in transformation experiments. DNA constructs capable of expressing the codeinone reductase genes were prepared in a binary vector containing a $^{35}S$-nptII selectable marker, and transformed into the *N. tabacum* and *P. somniferum* lines.

Successful transformation of these plant lines was achieved as judged by (a) regeneration of *N. tabacum* plants on medium containing 100 mg/l kanamycin indicating expression of the nptII selectable marker, which was verified by NPTII enzyme assays. Coexpression of the codeinone reductase gene was determined by RT-PCR (reverse transcriptase polymerase chain reaction) assay.

(b) successful selection of transformed cell cultures of *P. somniferum* using the same nptII selectable marker indicative of expression from the vector, followed by the generation of typeI and typeII embryogenic callus prior to the production of transformed plants.

Thus, the identification and cloning of genes for codeinone reductase from *P. somniferum* now provides a means by which alteration of the enzymatic step(s) involving this can be achieved. The overexpression of these sequences can be achieved using vectors which express one or more of the codeinone reductase alleles, while downregulation of general codeinone reductase activity or the activity of specific alleles can be achieved using vectors expressing antisense, ribozymes, plus-sense cosuppression or RNAi sequences from regions conserved between the codeinone reductase alleles or other sequences which are unique to each allele. These genes encoding the sense, antisense, ribozyme, RNAi or other such sequences can be delivered as transgenes stably integrated into the poppy genome or transiently in the form of a viral vector.

Although the invention has been described with reference to specific embodiments, modifications that are within the knowledge of those skilled in the art are also contemplated as being within the scope of the present invention.

REFERENCES

Amore, R., Koetter, P., Kuester, C., Cirlacy, M., and Hollenberg, C. P. (1991). Cloning and expression in *Saccharomyces cerevisiae* of the NAD(P)H-dependent xylose reductase-encoding gene (XYL1) from the xylose-assimilating yeast *Pichia stipitis*. Gene 109, 89–97.

An, G., Watson, B. D., Chiang, C. C. (1986). Transformation of tobacco, tomato, potato and *Arabidopsis thaliana* using a binary Ti vector system. Plant Physiology 81:301–305.

Bracher, D., and Kutchan, T. M. (1992). Strictosidine synthase from *Rauvolfia serpentina*: Analysis of a gene involved in indole alkaloid biosynthesis. Arch. Biochem. Biophys. 294, 717–723.

Brochmann-Hanssen, E. (1984). A second pathway for the terminal steps in the biosynthesis of morphine. Planta Med. 50, 343345.

De-Eknamkul, W., and Zenk, M. H. (1992). Purification and properties of 1,2-dehydroreticuline reductase from *Papaver somniferum* seedlings. Phytochemistry 31, 813–821.

Dittrich, H., and Kutchan, T. M. (1991). Molecular cloning, expression and induction of berberine bridge enzyme, an enzyme essential to the formation of benzophenanthridine alkaloids in the response of plants to pathogenic attack. Proc. Natl. Acad. Sci. USA 88, 9969–9973.

Eckerskorn, C., and Lottspelch, F. (1989). Internal amino acid sequence analysis of proteins separated by gel electrophoresis after tryptic digestion in polyacrylamide matrix. Chromatographia 28, 92–94.

Facchini, P. J., and De Luca, V. (1994). Differential and tissue-specific expression of a gene family for tyrosine/dopa decarboxylase in opium poppy. J. Biol. Chem. 269, 26684–26690.

French, C. E., Hailes, A. M., Rathbone, D. A., Long, M. T., Willey, D. L., and Bruce, N. C. (1995). Biological production of semisynthetic opiates using genetically engineered bacteria. Biotechnology 13. 674–676.

Frohman, M. A. (1993). Rapid amplification of complementary DNA ends for generation of full-length complementary DNAs: Thermal RACE. Methods Enzymol. 218, 340–356.

Gerardy, R. and, Zenk, M. H. (1993). Purification and characterization of salutaridine: NADPH 7-oxidoreductase from *Papaver somniferum*. Phytochemistry 34, 125–132.

Goliwitzer, I., Lenz, R., Hampp, N., and Zenk, M. H. (1993). The transformation of neopinone to codeinone in morphine biosynthesis proceeds non-enzymatically. Tetrahedron Lett. 34, 5703–5706.

Hooykaas, P. J. and Schilperoort, R. A. (1992). *Agrobacterium* and plant engineering. Plant Molec. Biol. 19:15–38.

Kutchan, T. M., Ayabe, S., and Coscia, C. J. (1985). Cytodifferentiation and *Papaver* alkaloid accumulation. In *The Chemistry and Biology of Isoquinoline Alkaloids*, (Phillipson, J. D., Roberts, M. F., Zenk, M. H., eds) Berlin: Springer-Verlag, pp. 281–294.

Kutchan, T. M., Rush, M. D., and Coscia, C A. (1986). Subcellular localization of alkaloids and dopamine in different vacuolar compartments of *Papaver bracteatum*. Plant Physiol. 81, 161–166.

Kutchan, T. M. (1998). Molecular genetics of plant alkaloid biosynthesis. In *The Alkaloids Vol.* 50, (Cordell, G., ed) San Diego: Academic Press, pp. 257–316.

Lenz, R., and Zenk, M. H. (1995a). Stereoselective reduction of codeinone, the penultimate enzymic step during morphine biosynthesis in *Papaver somniferum*. Tetrahedron Lett. 36, 2449–2452.

Lenz, R., and Zenk, M. H. (1995b). Purification and properties of codeinone reductase (NADPH) from *Papaver somniferum* cell cultures and differentiated plants. Eur. J. Biochem. 233, 132–139.

Linsmaier, E. M., and Skoog, F. (1965). Organic growth factor requirements of tobacco tissue cultures. Physiol. Plant. 18, 100–127.

Liras, P., Kasparian, S. S., and Umbreit, W. W. (1975). Enzymatic transformation of morphine by hydroxysteroid dehydrogenase from *Pseudomonas testosteroni*. Applied Microbiol. 30, 650–656.

Morjana, N. A., Lyons, C., and Flynn, T. G. (1989). Aldose reductase from human psoas muscle. Affinity labelling of an active site lysine by pyridoxal 5'-phosphate and pyridoxal 5'-diphospho-5'-adenosine. J. Biol. Chem. 264, 2912–2919.

Nessler, C. L., and Mahiberg, P. G. (1977). Ontogeny and cytochemistry of alkaloidal vessicles in laticifers of *Papaver somniferum* L. (Papaveraceae). Amer. J. Bot. 64, 541–551.

Nessler, C. L., and Mahiberg, P. G. (1978). Laticifer ultrastructure and differentiation in seedlings of *Papaver bracleatum* L., Population Arya 11 (Papaveraceae). Amer. J. Bot. 65, 978–983.

Nielsen, B., Röe, 1, and Brochmann-Hanssen, E. (1983). Oripavine—A new opium alkaloid. Plant Med. 48, 205–206.

Pauli, H. H., and Kutchan, T. M. (1998). Molecular cloning and functional heterologous expression of two alleles encoding (S)-N-methylcoclamine 3'-hydroxylase (CYP80B1), a new methyl jasmonate-inducible cytochrome P450 dependent monooxygenase of benzylisoquinoline alkaloid biosynthesis. Plant J. 13, 793–801.

Roberts, M. F., McCarthy, D., Kutchan, T. M., and Coscia, C. J. (1983). Localization of enzymes and alkaloidal metabolites in *Papaver* latex. Arch. Biochem. Biophys. 222,599–609.

Rosco, A., Pauli, H. H., Priesner, W., and Kutchan, T. M. (1997). Cloning and heterologous expression of cytochrome P450 reductases from the Papaveraceae. Arch. Biochem. Biophys. 348, 369–377.

Rush, M. D., Kutchan, T. M., and Coscia, C. J. (1985). Correlation of the appearance of morphinan alkaloids and laticifer cells in germinating *Papaver bracteatum* seedlings. Plant Cell Rep. 4, 237–240.

Sertürner, F. W. A. F. (1806). Darstellung der reinen Mohnsäure (Oplumsäure) nebst einer chemischen Untersuchung des Opiums mit vorzüglicher Hinsicht auf einen darin neu entdeckten Stoff und die dahin gehörigen Bemerckungen. J. Pharm. Ärzte Apotheker Chem. 14/1, 47–93.

Welle, R., Schroder, G., Schiltz, E, Grisebach, H., and Schroder, J. (1991). Induced plant responses to pathogen attack—Analysis and heterologous expression of the key enzyme in the biosynthesis of phytoalexins in soybean (*Glycine max* L. Merr. cv. Harosoy 63). Eur. J. Biochem. 196. 423–430.

Wieczorek, U., Nagakura, N., Sund, C., Jendrzejewski, S., and Zenk, M. H. (1986). Radioimmunoassay determination of six opium alkaloids and its application to plant screening. Phytochemistry 25, 2639–2646.

Ye, K., Ke, Y., Keshava, N., Shanks, J., Kapp, J. A., Tekmal, R. R., Petros, J., and Joshi. H. C. (1998). Opium alkaloid noscapine is an antitumor agent that arrests metaphase and induces apoptosis in dividing cells. Proc. Natl. Acad. Sci. USA 95, 16011606.

Yin, S.-J., Vagelopoulos, N., Lundquist, G., and Jornvall, H. (1991). *Pseudomonas* 3'-hydroxysteroid dehydrogenase—Primary structure and relationships to other steroid dehydrogenases. Eur. J. Biochem. 197, 7359–365.

Zenk, M. H. (1994). Über das Opium, das den Schrnerz besiegt und die Sucht weckt. Bayerische Akademie der Wissenschaften, Jahrbuch 1993, München: C. H. Beck'sche Verlagsbuchhandlung, pp. 98–126.

The invention claimed is:

1. An isolated and purified polynucleotide, encoding a codeinone reductase enzyme from an alkaloid poppy plant, wherein said codeinone reductase enzyme comprises SEQ ID NO: 26.

2. A polynucleotide according to claim 1, selected from the group consisting of genomic DNA, cDNA or synthetic DNA.

3. A polynucleotide according to claim 1, lacking the native leader sequences or any of the 5' or 3' untranslated regions of the polynucleotide.

4. A polynucleotide according to claim 3, wherein the native leader sequences or any of the 5' or 3' untranslated regions are replaced with exogenous regulatory sequences which regulate enhanced expression of the polynucleotide in an expression system.

5. A polynucleotide according to claim 1, which encodes a codeinone reductase enzyme from *Papaver somniferum*.

6. A polynucleotide according to claim 1, which is a synthetic polynucleotide comprising one or more codons preferred for expression in plant cells.

7. An isolated and purified polynucleotide which codes for prokaryotic or eukaryotic expression of a codeinone reductase enzyme from an alkaloid poppy plant, wherein the polynucleotide is expressed in an environment selected from the group consisting of the extracellular environment, an intracellular membrane compartment, intracellular cytoplasmic compartment or combinations, and wherein said codeinone reductase enzyme comprises SEQ ID NO: 26.

8. A polynucleotide according to claim 7, comprising a nucleotide sequence which directs expression of the codeinone reductase enzyme with respect to a particular cellular compartment or the extracellular environment.

9. An isolated and purified polynucleotide encoding a codeinone reductase enzyme from *Papaver somniferum*, selected from the group consisting of:
the polynucleotide sequence of SEQ ID NO: 20;
a polynucleotide sequence which hybridizes under stringent conditions to complementary sequences of SEQ ID NO: 20, wherein said polynucleotide sequence is at least 95% identical to SEQ ID NO: 20; and
a polynucleotide sequence which is an allele of SEQ ID NO: 20, wherein said polynucleotide sequence is at least 95% identical to SEQ ID NO: 20; wherein said polynucleotide codes for a codeinone reductase enzyme which has codeinone reductase activity.

10. A recombinant DNA construct comprising the polynucleotide according to claim 1.

11. A DNA construct according to claim 10, which is a viral or plasmid vector.

12. A DNA construct according to claim 10 capable of directing prokaryotic or eukaryotic expression of the polynucleotide encoding a codeinone reductase enzyme.

13. A DNA construct according to claim 10, comprising a promoter suitable to control the expression of the polynucleotide.

14. A DNA construct according to claim 13, wherein the promoter is endogenous.

15. A DNA construct according to claim 13, wherein the promoter is derived from nos, cauliflower mosaic virus or subterranean clover mosaic virus.

16. A DNA construct according to claim 11, wherein the plasmid is pCAL-c.

17. A DNA construct according to claim 11, wherein the plasmid is pGEM-T.

18. A DNA construct according to claim 11, wherein the plasmid is pFastBacI.

19. A method for preparing plants which overexpress a codeinone reductase enzyme, comprising transfecting or transforming a plant cell, a plant part or a plant, with the polynucleotide according to claim 1.

20. A method according to claim 19, wherein the plant is an alkaloid poppy plant.

21. A method according to claim 20, wherein the poppy plant is *Papaver somniferum*.

22. The isolated polynucleotide sequence encoding codeinone reductase comprised in microbial deposit DSM 12737.

23. A method for transfecting or transforming a plant, comprising transfecting or transforming a plant cell, plant part, or plant with a polynucleotide according to claim 1.

24. A method for transfecting or transforming a plant, comprising transfecting or transforming a plant cell, plant part, or plant with a polynucleotide sequence comprising SEQ ID NO: 20 and wherein said polynucleotide codes for a codeinone reductase enzyme which has codeinone reductase activity.

25. A method for transfecting or transforming a plant, comprising transfecting or transforming a plant cell, plant part, or plant with a polynucleotide sequence which hybridizes under stringent conditions to the complementary sequences of SEQ ID NO: 20, wherein said polynucleotide sequence is at least 95% identical to SEQ ID NO: 20, and wherein said polynucleotide codes for a codeinone reductase enzyme which has codeinone reductase activity.

26. A method for transfecting or transforming a plant, comprising transfecting or transforming a plant cell, plant part, or plant with a polynucleotide sequence which is an allele of SEQ ID NO: 20, wherein said polynucleotide sequence is at least 95% identical to SEQ ID NO: 20, and wherein said polynucleotide codes for a codeinone reductase enzyme which has codeinone reductase activity.

27. An isolated polynucleotide sequence which contains at least 95% homology to SEQ ID NO: NO: 20 and wherein said polynucleotide codes for a codeinone reductase enzyme which has codeinone reductase activity.

* * * * *

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (3)..(3)
<223> OTHER INFORMATION: n = A or G
<220> FEATURE:
<221> NAME/KEY: misc_feature
<222> LOCATION: (6)..(6)
<223> OTHER INFORMATION: n = T or C
<220> FEATURE:
<221> NAME/KEY: misc_feature
<222> LOCATION: (9)..(9)
<223> OTHER INFORMATION: n = T or C
<220> FEATURE:
<221> NAME/KEY: misc_feature
<222> LOCATION: (12)..(12)
<223> OTHER INFORMATION: n = A or C or T
<220> FEATURE:
<221> NAME/KEY: misc_feature
<222> LOCATION: (15)..(15)
<223> OTHER INFORMATION: n = T or G
<220> FEATURE:
<221> NAME/KEY: misc_feature
<222> LOCATION: (18)..(18)
<223> OTHER INFORMATION: n = T or C

<400> SEQUENCE: 1
ganctnttna tnacntcnaa                                            20

<210> SEQ ID NO 2
<211> LENGTH: 26
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (3)..(3)
<223> OTHER INFORMATION: n = T or C
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (8)..(8)
<223> OTHER INFORMATION: n = T or G
<220> FEATURE:
<221> NAME/KEY: misc_feature
<222> LOCATION: (9)..(9)
<223> OTHER INFORMATION: n = T or A
```

```
<220> FEATURE:
<221> NAME/KEY: misc_feature
<222> LOCATION: (12)..(12)
<223> OTHER INFORMATION: n = i
<220> FEATURE:
<221> NAME/KEY: misc_feature
<222> LOCATION: (24)..(24)
<223> OTHER INFORMATION: n = G or A

<400> SEQUENCE: 2
ttnccncnng cnactgcaat ctgntg                                   26

<210> SEQ ID NO 3
<211> LENGTH: 21
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (4)..(4)
<223> OTHER INFORMATION: n = T or C
<220> FEATURE:
<221> NAME/KEY: misc_feature
<222> LOCATION: (10)..(10)
<223> OTHER INFORMATION: n = T or C
<220> FEATURE:
<221> NAME/KEY: misc_feature
<222> LOCATION: (16)..(16)
<223> OTHER INFORMATION: n = C or G
<220> FEATURE:
<221> NAME/KEY: misc_feature
<222> LOCATION: (19)..(19)
<223> OTHER INFORMATION: n = i

<400> SEQUENCE: 3
catntccacn tgattnacna c                                        21

<210> SEQ ID NO 4
<211> LENGTH: 29
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (3)..(3)
<223> OTHER INFORMATION: n = i
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (9)..(9)
<223> OTHER INFORMATION: n = C or T
<220> FEATURE:
<221> NAME/KEY: misc_feature
<222> LOCATION: (12)..(12)
<223> OTHER INFORMATION: n = A or G
<220> FEATURE:
<221> NAME/KEY: misc_feature
<222> LOCATION: (15)..(15)
<223> OTHER INFORMATION: n = i
<220> FEATURE:
<221> NAME/KEY: misc_feature
<222> LOCATION: (18)..(18)
<223> OTHER INFORMATION: n = A or G
<220> FEATURE:
<221> NAME/KEY: misc_feature
<222> LOCATION: (22)..(22)
<223> OTHER INFORMATION: n = A or T
<220> FEATURE:
<221> NAME/KEY: misc_feature
<222> LOCATION: (23)..(23)
```

```
<223> OTHER INFORMATION: n = G or C
<220> FEATURE:
<221> NAME/KEY: misc_feature
<222> LOCATION: (24)..(24)
<223> OTHER INFORMATION: n = i
<220> FEATURE:
<221> NAME/KEY: misc_feature
<222> LOCATION: (27)..(27)
<223> OTHER INFORMATION: n = i

<400> SEQUENCE: 4
gtngtnaanc angtnganat gnnccnac                                          29

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
atggagagta atggtgtacc t                                                 21

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
gacagtcctc acttaccatc t                                                 21

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
atggctagca tggagagtaa tggtgtacct atg                                    33

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
aagggatcca tccttctcat cccagaactc ttc                                    33

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 9

Xaa Leu Gln Glu Leu Met Ala
1               5
```

```
<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Val Leu His Gln Ile Ala Val Ala Arg Gly Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asp Asp Asp Glu Leu Phe Ile Thr Ser Lys
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Ile Pro Asp Val Val Asn Gln Val Glu Met Ser Pro Thr Leu Gly Gln
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

Xaa Val Asn Glu Ile Pro Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Val Ala Gln Val
1               5

<210> SEQ ID NO 15
<211> LENGTH: 10
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Ile Phe Asp Asn Xaa Leu Thr Ala Glu Asp
1               5                   10

<210> SEQ ID NO 16
<211> LENGTH: 230
<212> TYPE: PRT
<213> ORGANISM: Alfalfa

<400> SEQUENCE: 16

Lys Gln Gly Tyr Arg His Phe Asp Thr Ala Ala Ala Tyr Gly Ser Glu
1               5                   10                  15

Gln Ala Leu Gly Glu Ala Leu Lys Glu Ala Ile Glu Leu Gly Leu Val
            20                  25                  30

Thr Arg Glu Glu Leu Phe Val Thr Ser Lys Leu Trp Val Thr Glu Asn
        35                  40                  45

His Pro His Leu Val Ile Pro Ala Leu Gln Lys Ser Leu Lys Thr Leu
    50                  55                  60

Gln Leu Asp Tyr Leu Asp Leu Tyr Leu Ile His Trp Pro Leu Ser Ser
65                  70                  75                  80

Gln Pro Gly Lys Phe Ser Phe Pro Ile Asp Val Ala Asp Leu Leu Pro
                85                  90                  95

Phe Asp Val Lys Gly Val Trp Glu Ser Met Glu Glu Ser Leu Lys Leu
            100                 105                 110

Gly Leu Thr Lys Ala Ile Gly Val Ser Asn Phe Ser Val Lys Lys Leu
        115                 120                 125

Glu Asn Leu Leu Ser Val Ala Thr Val Leu Pro Ala Val Asn Gln Val
    130                 135                 140

Glu Met Asn Leu Ala Trp Gln Gln Lys Lys Leu Arg Glu Phe Cys Asn
145                 150                 155                 160

Ala Asn Gly Ile Val Leu Thr Ala Phe Ser Pro Leu Arg Lys Gly Ala
                165                 170                 175

Ser Arg Gly Pro Asn Glu Val Met Glu Asn Asp Met Leu Lys Glu Ile
            180                 185                 190

Ala Asp Ala His Gly Lys Ser Val Ala Gln Ile Ser Leu Arg Trp Leu
        195                 200                 205

Tyr Glu Gln Gly Val Thr Phe Val Pro Lys Ser Tyr Asp Lys Glu Arg
    210                 215                 220

Met Asn Gln Asn Leu Cys
225                 230

<210> SEQ ID NO 17
<211> LENGTH: 230
<212> TYPE: PRT
<213> ORGANISM: Glycyrrhiza

<400> SEQUENCE: 17

Lys Gln Gly Tyr Arg His Phe Asp Thr Ala Ala Ala Tyr Gly Ser Glu
1               5                   10                  15

Thr Ala Leu Gly Glu Ala Leu Lys Glu Ala Arg Asp Leu Gly Leu Val
            20                  25                  30

Thr Arg Glu Glu Leu Phe Val Thr Ser Lys Leu Trp Val Thr Glu Asn
```

```
                35                  40                  45
His Pro His Leu Val Ile Pro Ala Leu Arg Lys Ser Leu Glu Thr Leu
         50                  55                  60
Gln Leu Glu Tyr Leu Asp Leu Tyr Leu Ile His Trp Pro Leu Ser Ser
 65                  70                  75                  80
Gln Pro Gly Lys Phe Ser Phe Pro Ile Gln Val Glu Asp Leu Leu Pro
                 85                  90                  95
Phe Asp Val Lys Gly Val Trp Glu Ser Met Glu Glu Cys Leu Lys Leu
                100                 105                 110
Gly Leu Thr Lys Ala Ile Gly Val Ser Asn Phe Ser Val Lys Lys Leu
                115                 120                 125
Gln Asn Leu Leu Ser Val Ala Thr Ile Arg Pro Ala Val Val Gln Val
130                 135                 140
Glu Met Asn Leu Ala Trp Gln Gln Lys Lys Leu Arg Glu Phe Cys Thr
145                 150                 155                 160
Ala Asn Gly Ile Val Leu Thr Ala Phe Ser Pro Leu Arg Lys Gly Ala
                165                 170                 175
Ser Arg Gly Pro Asn Glu Val Met Glu Asn Asp Met Leu Lys Gly Ile
                180                 185                 190
Ala Glu Ala His Gly Lys Ser Ile Ala Gln Val Ser Leu Arg Trp Leu
                195                 200                 205
Tyr Glu Gln Gly Val Thr Phe Val Ala Lys Ser Tyr Asp Lys Glu Arg
                210                 215                 220
Met Asn Gln Asn Leu Gln
225                 230

<210> SEQ ID NO 18
<211> LENGTH: 230
<212> TYPE: PRT
<213> ORGANISM: Soybean

<400> SEQUENCE: 18

Lys Gln Gly Tyr Arg His Phe Asp Thr Ala Ala Tyr Gly Ser Glu
 1               5                  10                  15
Gln Ala Leu Gly Glu Ala Leu Lys Glu Ala Ile His Leu Gly Leu Val
                 20                  25                  30
Arg Ser Gln Asp Leu Phe Val Thr Ser Lys Leu Trp Val Thr Glu Asn
                 35                  40                  45
His Pro His Leu Val Leu Pro Ala Leu Arg Lys Ser Leu Lys Thr Leu
         50                  55                  60
Gln Leu Glu Tyr Leu Asp Leu Tyr Leu Ile His Trp Pro Leu Ser Ser
 65                  70                  75                  80
Gln Pro Gly Lys Phe Ser Phe Pro Ile Glu Val Glu Asp Leu Leu Pro
                 85                  90                  95
Phe Asp Val Lys Gly Val Trp Glu Ser Met Glu Glu Cys Gln Lys Leu
                100                 105                 110
Gly Leu Thr Lys Ala Ile Gly Val Ser Asn Phe Ser Val Lys Lys Leu
                115                 120                 125
Gln Asn Leu Leu Ser Val Ala Thr Ile Arg Pro Val Val Asp Gln Val
130                 135                 140
Glu Met Asn Leu Ala Trp Gln Gln Lys Lys Leu Arg Glu Phe Cys Lys
145                 150                 155                 160
Glu Asn Gly Ile Ile Val Thr Ala Phe Ser Pro Leu Arg Lys Gly Ala
                165                 170                 175
```

Ser Arg Gly Pro Asn Glu Val Met Glu Asn Asp Val Leu Lys Glu Ile
            180                 185                 190

Ala Glu Ala His Gly Lys Ser Ile Ala Gln Val Ser Leu Arg Trp Leu
            195                 200                 205

Tyr Glu Gln Gly Val Thr Phe Val Pro Lys Ser Tyr Asp Lys Glu Arg
        210                 215                 220

Met Asn Gln Asn Leu His
225                 230

<210> SEQ ID NO 19
<211> LENGTH: 44
<212> TYPE: PRT
<213> ORGANISM: Opium poppy

<400> SEQUENCE: 19

Glu Leu Phe Ile Thr Ser Lys Leu Gln Glu Leu Met Ala Ile Pro Asp
1               5                   10                  15

Val Val Asn Gln Val Glu Met Ser Pro Thr Leu Val Leu His Gln Ile
            20                  25                  30

Ala Val Ala Arg Gly Lys Val Asn Glu Ile Pro Lys
        35                  40

<210> SEQ ID NO 20
<211> LENGTH: 1035
<212> TYPE: DNA
<213> ORGANISM: Papaver somniferum

<400> SEQUENCE: 20
gaaaaatgga gagtaatggt gtacctatga tcactctcag ttccggcatt cggatgcctg      60
ctttaggtat gggaacagct gaaacaatgg taaaggaac agaaagagag aaattggcgt     120
ttttgaaagc gatagaggtc ggttacagac acttcgatac agctgctgca taccaaactg    180
aagagtgtct tggtgaagct atagctgaag cacttcaact tggtctaata aaatctcgag    240
atgaactctt catcacttcc aagctctggt gcgctgatgc tcacgctgat cttgtcctcc    300
ctgctcttca gaattctctg aggaatctta aattggacta tcttgatcta tatttgatac    360
accatccggt aagcttgaag ccagggaagt tgttaacga ataccaaag gatcatatcc      420 ttccaatgga ctacaaatct gtatgggcag ccatggaaga gtgtcagacc cttggcttca    480
ctagggcaat cggggtctgt aatttctcat gcaaaaggct tcaagagttg atggaaacag    540
ccaacagccc tccagttgtg aatcaagtgg agatgagccc gactttacat caaaaaaatc    600
tgagggaata ttgcaaggcc aataatatca tgatcaccgc acactcagtt ttgggagccg    660
taggtgccgc ctgggcacc aatgcagtta tgcattctaa ggtgcttcac cagattgctg     720
tggccagagg aaaatctgtt gcccaggtta gtatgagatg ggtttaccag caaggcgcga    780
gtcttgtggt gaaagtttc aatgaagcga ggatgaagga aaaccttaag atatttgatt     840
gggaactaac ggcagaagac atggaaaaga tcagtgagat tccacaatct agaacaagct    900
ctgctgcttt cttgttatca ccgactggac ctttcaaaac tgaagaagag ttctgggatg    960
agaaggattg aaacatcaat tatagatggt aagtgaggac tgtcaaaaaa gtaatcagtt   1020
tttccctccg ttttg                                                    1035

<210> SEQ ID NO 21
<211> LENGTH: 966
<212> TYPE: DNA
<213> ORGANISM: Papaver somniferum

<400> SEQUENCE: 21

```
atggagagta atggtgtacc tatgatcact ctcagttccg gcattcggat gcctgcttta      60
ggtatgggaa cagttgaaac aatggaaaag ggaacagaaa gagagaaatt ggcgttttg     120
aatgcgatag aggtcggtta cagacacttc gatacagctg ctgcatacca aagtgaagag    180
tgtcttggtg aagctatagc tgaagcactt caacttggtt taataaaatc tcgagatgaa    240
ctcttcatca cttccaagct ctggtgcgct gatgctcacg ctgatcttgt cctccctgct    300
cttcagaatt ctctgaggaa tctcaaattg gagtacttg atctatattt gatacaccat     360
ccggtaagct tgaagccagg gaagcttgtt aacgaaatac caaggatca tattcttcca     420
atggactaca atctgtatg ggcagccatg gaagagtgtc agacccttgg cttcactagg     480
gcaatcggtg tcagtaattt ctcatgcaaa agcttcaag agttgatggc aacagccaag     540
atccctccag ttgtgaatca gtggagatg agcccgactt acatcaaaa aaatctgagg     600
gaatattgca aggccaataa tatcatgatc actgcacact cggttttggg agccataggt    660
gctccatggg gcagcaacgc agttatggat tctaaggtgc ttcaccagat tgctgtggca    720
agaggaaaat ctgttgccca ggttagtatg agatgggttt accagcaagg cgcgagtctt    780
gtggtgaaaa gtttcaatga agcgaggatg aaggaaaacc ttaagatatt tgattcggaa    840
ctaacggcag aagatatgga aaagatcagt gagattccgc aatctagaac aagctctgct    900
gatttcttgt tatcaccgac tggacctttc aaaactgaag aagagttctg ggatgagaag    960
gattga                                                                966
```

<210> SEQ ID NO 22
<211> LENGTH: 966
<212> TYPE: DNA
<213> ORGANISM: Papaver somniferum

<400> SEQUENCE: 22

```
atggagagta atggtgtacc tatgatcact ctcagttccg gcattcggat gcctgcttta      60
ggtatgggaa cagctgaaac aatggtaaaa ggaacagaaa gagagaaatt ggcgttttg     120
aaagcgatag aggtcggtta cagacacttc gatacagctg ctgcatacca aagtgaagag    180
tgtcttggtg aagctatagc tgaagcactt caacttggtc taataaaatc tcgagatgaa    240
ctcttcatca cttccaagct ctggtgcgct gatgctcacg ctgatcttgt cctccctgct    300
cttcagaatt ctctgaggaa tcttaaattg gactatcttg atctatattt gatacaccat    360
ccggtaagct tgaagccagg gaagtttgtt aacgaaatac caaggatca tatccttcca     420
atggactaca atctgtatg ggcagccatg gaagagtgtc agacccttgg cttcactagg     480
gcaatcgggg tctgtaattt ctcatgcaaa agcttcaag agttgatggc agcagccaag     540
atccctccag ttgtgaatca gtggagatg agcccgactt acatcaaaa aaatctgagg     600
gaatattgca aggccaataa tatcatgatc actgcacact cggttttggg agccatatgt    660
gctccatggg gcagcaatgc agttatggat tctaaggtgc ttcaccagat tgctgtggca    720
agaggaaaat ctgttgccca ggttagtatg agatgggttt accagcaagg cgcgagtcta    780
gtggtgaaaa gtttcaatga agggaggatg aaggaaaacc ttaagatatt tgattgggaa    840
ctaacggcag agaatatgga aaagatcagt gagattccgc aatctagaac aagctctgct    900
gatttcttgt tatcaccgac tggacctttc aaaactgaag aagagttctg ggatgagaag    960
gattga                                                                966
```

<210> SEQ ID NO 23
<211> LENGTH: 966
<212> TYPE: DNA
<213> ORGANISM: Papaver somniferum

<400> SEQUENCE: 23

| | | | | | |
|---|---|---|---|---|---|
| atggagagta | atggtgtacc | tatgatcact | ctcagttccg | gcattcggat | gcctgcttta | 60 |
| ggtatgggaa | cagctgaaac | aatggtaaaa | ggaacagaaa | gagagaaatt | ggcgttttttg | 120 |
| aaagcgatag | aggtcggtta | cagacacttc | gatacagctg | ctgcatacca | aagtgaagag | 180 |
| tgtcttggtg | aagctatagc | tgaagcactt | caacttggtt | taataaaatc | tcgagatgaa | 240 |
| ctcttcatca | cttccaagct | ctggtgcgct | gatgctcacg | ctgatcttgt | cctccctgct | 300 |
| cttcagaatt | ctctgaggaa | tctcaaattg | gagtatcttg | atctatattt | gatacaccat | 360 |
| ccggtaagct | tgaagccagg | gaaatttgtt | aacgaaatac | caaggatca | tattcttcca | 420 |
| atggactaca | atctgtatg | gcagccatg | gaagagtgtc | agacccttgg | cttcactagg | 480 |
| gcaatcggtg | tcagtaattt | ctcatgcaaa | agcttcaag | agttgatggc | agcagccaag | 540 |
| atccctccag | ttgtgaatca | agtggagatg | agccctactt | tacatcaaaa | aaatctgagg | 600 |
| gaatattgca | aggccaataa | tatcatgatc | actgcacact | cggttttggg | agccataggt | 660 |
| gctccatggg | gcagcaatgc | agttatggat | tctaaggtgc | ttcaccagat | tgctgtggca | 720 |
| agaggaaaat | ctgttgccca | ggttagtatg | agatgggttt | accagcaagg | cgcgagtctt | 780 |
| gtggtgaaaa | gtttcaatga | agggaggatg | aaggaaaacc | ttaagatatt | tgattgggaa | 840 |
| ctaacggcag | aagatatgga | aaagatcagt | gagattccgc | aatctagaac | aagctctgct | 900 |
| gctttcttgt | tatcaccgac | tggacctttc | aaaactgaag | aagagttctg | ggatgagaag | 960 |
| gattga | | | | | 966 |

<210> SEQ ID NO 24
<211> LENGTH: 154
<212> TYPE: DNA
<213> ORGANISM: Papaver somniferum

<400> SEQUENCE: 24

| | | | | | |
|---|---|---|---|---|---|
| tgtggtgaat | caggtggaga | gtgtggccgac | tttacatcaa | aaaaatctga | gggaatattg | 60 |
| caaggccaat | aatatcatga | tcactgcaca | ctcggttttg | ggagccatag | gtgctccatg | 120 |
| gggcagcaat | gcagttatgg | attctaaggt | gctt | | | 154 |

<210> SEQ ID NO 25
<211> LENGTH: 291
<212> TYPE: DNA
<213> ORGANISM: Papaver somniferum

<400> SEQUENCE: 25

| | | | | | |
|---|---|---|---|---|---|
| ctctggtgcg | ctgatgctca | cgctgatctt | gtcctccctg | ctcttcagaa | ttctctgagg | 60 |
| aatctgaaat | tggactacct | tgatctatat | ttgatacacc | atccggtaag | cttgaagcca | 120 |
| gggaagcttg | ttaacgaaat | accaaaggat | catattcttc | caatggacta | caaatctgta | 180 |
| tgggcagcca | tggaagagtg | tcagaccctt | ggcttcacta | gggcaatcgg | tgtcagtaat | 240 |
| ttctcatgca | aaaagcttca | agagttgatg | gcaacagcca | agatccctcc | a | 291 |

<210> SEQ ID NO 26
<211> LENGTH: 321
<212> TYPE: PRT
<213> ORGANISM: Papaver somniferum -continued

```
<400> SEQUENCE: 26

Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Tyr Gln Thr Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Arg Leu Gln Glu Leu Met
                165                 170                 175

Glu Thr Ala Asn Ser Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Val Gly Ala Ala Trp Gly
    210                 215                 220

Thr Asn Ala Val Met His Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Ala Arg Met Lys Glu
            260                 265                 270

Asn Leu Lys Ile Phe Asp Trp Glu Leu Thr Ala Glu Asp Met Glu Lys
        275                 280                 285

Ile Ser Glu Ile Pro Gln Ser Arg Thr Ser Ser Ala Ala Phe Leu Leu
    290                 295                 300

Ser Pro Thr Gly Pro Phe Lys Thr Glu Glu Glu Phe Trp Asp Glu Lys
305                 310                 315                 320

Asp

<210> SEQ ID NO 27
<211> LENGTH: 321
<212> TYPE: PRT
<213> ORGANISM: Papaver somniferum

<400> SEQUENCE: 27

Met Glu Ser Asn Gly Val Pro Met Ile Thr Leu Ser Ser Gly Ile Arg
1               5                   10                  15

Met Pro Ala Leu Gly Met Gly Thr Val Glu Thr Met Glu Lys Gly Thr
            20                  25                  30

Glu Arg Glu Lys Leu Ala Phe Leu Asn Ala Ile Glu Val Gly Tyr Arg
```

```
                    35                  40                  45
His Phe Asp Thr Ala Ala Tyr Gln Ser Glu Glu Cys Leu Gly Glu
            50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Glu Tyr
            100                 105                 110

Leu Asp Leu Tyr Leu Ile His His Pro Val Ser Leu Lys Pro Gly Lys
            115                 120                 125

Leu Val Asn Glu Ile Pro Lys Asp His Ile Leu Pro Met Asp Tyr Lys
            130                 135                 140

Ser Val Trp Ala Ala Met Glu Glu Cys Gln Thr Leu Gly Phe Thr Arg
145                 150                 155                 160

Ala Ile Gly Val Ser Asn Phe Ser Cys Lys Lys Leu Gln Glu Leu Met
                165                 170                 175

Ala Thr Ala Lys Ile Pro Pro Val Val Asn Gln Val Glu Met Ser Pro
            180                 185                 190

Thr Leu His Gln Lys Asn Leu Arg Glu Tyr Cys Lys Ala Asn Asn Ile
            195                 200                 205

Met Ile Thr Ala His Ser Val Leu Gly Ala Ile Gly Ala Pro Trp Gly
            210                 215                 220

Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Ala Arg Met Lys Glu
            260                 265                 270

Asn Leu Lys Ile Phe Asp Ser Glu Leu Thr Ala Glu Asp Met Glu Lys
            275                 280                 285

Ile Ser Glu Ile Pro Gln Ser Arg Thr Ser Ser Ala Asp Phe Leu Leu
            290                 295                 300

Ser Pro Thr Gly Pro Phe Lys Thr Glu Glu Glu Phe Trp Asp Glu Lys
305                 310                 315                 320

Asp

<210> SEQ ID NO 28
<211> LENGTH: 321
<212> TYPE: PRT
<213> ORGANISM: Papaver somniferum

<400> SEQUENCE: 28

Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
            35                  40                  45

His Phe Asp Thr Ala Ala Tyr Gln Ser Glu Glu Cys Leu Gly Glu
            50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
```

```
                85                  90                  95
Val Leu Pro Ala Leu Gln Asn Ser Leu Arg Asn Leu Lys Leu Asp Tyr
            100                 105                 110
Leu Asp Leu Tyr Leu Ile His His Pro Val Ser Leu Lys Pro Gly Lys
            115                 120                 125
Phe Val Asn Glu Ile Pro Lys Asp His Ile Leu Pro Met Asp Tyr Lys
            130                 135                 140
Ser Val Trp Ala Ala Met Glu Glu Cys Gln Thr Leu Gly Phe Thr Arg
145                 150                 155                 160
Ala Ile Gly Val Cys Asn Phe Ser Cys Lys Lys Leu Gln Glu Leu Met
                165                 170                 175
Ala Ala Ala Lys Ile Pro Pro Val Val Asn Gln Val Glu Met Ser Pro
            180                 185                 190
Thr Leu His Gln Lys Asn Leu Arg Glu Tyr Cys Lys Ala Asn Asn Ile
            195                 200                 205
Met Ile Thr Ala His Ser Val Leu Gly Ala Ile Cys Ala Pro Trp Gly
            210                 215                 220
Ser Asn Ala Val Met Asp Ser Lys Val Leu His Gln Ile Ala Val Ala
225                 230                 235                 240
Arg Gly Lys Ser Val Ala Gln Val Ser Met Arg Trp Val Tyr Gln Gln
                245                 250                 255
Gly Ala Ser Leu Val Val Lys Ser Phe Asn Glu Gly Arg Met Lys Glu
            260                 265                 270
Asn Leu Lys Ile Phe Asp Trp Glu Leu Thr Ala Glu Asn Met Glu Lys
            275                 280                 285
Ile Ser Glu Ile Pro Gln Ser Arg Thr Ser Ser Ala Asp Phe Leu Leu
290                 295                 300
Ser Pro Thr Gly Pro Phe Lys Thr Glu Glu Glu Phe Trp Asp Glu Lys
305                 310                 315                 320
Asp

<210> SEQ ID NO 29
<211> LENGTH: 321
<212> TYPE: PRT
<213> ORGANISM: Papaver somniferum

<400> SEQUENCE: 29

Met Glu Ser Asn Gly Val Pro Met Ile Thr Leu Ser Ser Gly Ile Arg
1               5                   10                  15
Met Pro Ala Leu Gly Met Gly Thr Ala Glu Thr Met Val Lys Gly Thr
            20                  25                  30
Glu Arg Glu Lys Leu Ala Phe Leu Lys Ala Ile Glu Val Gly Tyr Arg
        35                  40                  45
His Phe Asp Thr Ala Ala Ala Tyr Gln Ser Glu Glu Cys Leu Gly Glu
    50                  55                  60
Ala Ile Ala Glu Ala Leu Gln Leu Gly Leu Ile Lys Ser Arg Asp Glu
65                  70                  75                  80
Leu Phe Ile Thr Ser Lys Leu Trp Cys Ala Asp Ala His Ala Asp Leu
                85                  90                  95
Val Leu Pro Ala Leu Gln Asn Ser Leu Arg Asn Leu Lys Leu Glu Tyr
            100                 105                 110
Leu Asp Leu Tyr Leu Ile His His Pro Val Ser Leu Lys Pro Gly Lys
            115                 120                 125
Phe Val Asn Glu Ile Pro Lys Asp His Ile Leu Pro Met Asp Tyr Lys
```

-continued

```
                130                 135                 140
Ser Val Trp Ala Ala Met Glu Glu Cys Gln Thr Leu Gly Phe Thr Arg
145                 150                 155                 160

Ala Ile Gly Val Ser Asn Phe Ser Cys Lys Lys Leu Gln Glu Leu Met
                165                 170                 175

Ala Ala Ala Lys Ile Pro Pro Val Val Asn Gln Val Glu Met Ser Pro
                180                 185                 190

Thr Leu His Gln Lys Asn Leu Arg Glu Tyr Cys Lys Ala Asn Asn Ile
            195                 200                 205

Met Ile Thr Ala His Ser Val Leu Gly Ala Ile Gly Ala Pro Trp Gly
        210                 215                 220

Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Gly Arg Met Lys Glu
                260                 265                 270

Asn Leu Lys Ile Phe Asp Trp Glu Leu Thr Ala Glu Asp Met Glu Lys
            275                 280                 285

Ile Ser Glu Ile Pro Gln Ser Arg Thr Ser Ser Ala Ala Phe Leu Leu
        290                 295                 300

Ser Pro Thr Gly Pro Phe Lys Thr Glu Glu Glu Phe Trp Asp Glu Lys
305                 310                 315                 320

Asp
```